United States Patent [19]

Powell et al.

[11] Patent Number: 6,150,170
[45] Date of Patent: *Nov. 21, 2000

[54] METHOD FOR INTRODUCING AND EXPRESSING GENES IN ANIMAL CELLS, AND LIVE INVASIVE BACTERIAL VECTORS FOR USE IN THE SAME

[75] Inventors: Robert J. Powell; George K. Lewis, both of Baltimore; David M. Hone, Ellicott City, all of Md.

[73] Assignee: University of Maryland at Baltimore, Baltimore, Md.

[ * ] Notice: This patent is subject to a terminal disclaimer.

[21] Appl. No.: 09/126,220

[22] Filed: Jul. 30, 1998

Related U.S. Application Data

[63] Continuation of application No. 08/433,790, May 3, 1998, Pat. No. 5,877,159.

[51] Int. Cl.$^7$ .......................... C12N 15/63; C12N 15/00; C12N 5/00; A01N 43/04; A61K 31/70
[52] U.S. Cl. .......................... 435/455; 435/455; 435/472; 435/480; 435/69.1; 435/320.1; 514/44; 424/184.1; 424/93.1; 424/93.21; 424/93.4
[58] Field of Search .............................. 514/44; 435/455, 435/472, 480, 69.1, 320.1; 424/184.1, 93.1, 93.21, 93.4

[56] References Cited

U.S. PATENT DOCUMENTS

| | | | |
|---|---|---|---|
| 4,888,170 | 12/1989 | Curtiss, III | 424/93 |
| 5,824,538 | 10/1998 | Branstrom | 435/252.1 |
| 5,877,159 | 3/1999 | Powell | 514/44 |

FOREIGN PATENT DOCUMENTS

| | | |
|---|---|---|
| 0211543 | 2/1987 | European Pat. Off. . |
| 0441071 | 8/1991 | European Pat. Off. . |
| 2564482 | 11/1985 | France . |

OTHER PUBLICATIONS

Eck & Wilson, 'Game–Based Therapy' in Goodman & Gilman's The Pharmacological Basis of Therapeutics, McGraw–Hill: New York, Ninth Edition, pp. 77–101, 1996.
Marschall et al, *Cell. Mol. Neurobiol.*, 14(5):523–538 (1994).
Biasolo et al, *J. Virol.*, 70(4):2154–2161 (1996).
Lu et al, *Cancer Gene Ther.*, 1(4):267–277 (1994).
Sizemore et al, "Attenuated Shigella as a DNA Delivery Vehicle for DNA–Mediated Immunization", *Science*, 270:289–302 (1995).
Slauch et al, *Methods in Enzymology*, 235:481–492 (1994).
Cirillo et al, *Clinical Infectious Diseases*, 20:1001–1009 (1995).
Cárdenas et al., *Vaccine*, 11(2):126–135 (1993).
Aggarwal et al, *J. Exp. Med.*, 175(4):1095–1090 (1990).
Noriega et al, *Infect. Immun.*, 62(11):5168–5172 (1994).
Conry et al, *Cancer Res.*, 55:1397–1400 (1995).
Ulmer et al, *Science*, 259:1745–1749 (1993).
Wolff et al, *Science*, 257:1465–1468 (1990).
Gillies et al, *Cell*, 33:717–728 (1983).
Sandri–Goldin et al, *Mol. Cell. Biol.*, 1(8):743–752 (1981).
Schaffner et al, *Proc. Natl. Acad. Sci. USA*, 77(4):2163–2167 (1988).
Marshall, *Science*, 269:1050–1055 (1995).
Culver et al, *TIG*, 10(5):174–178 (1994).
Miller et al, *FASEB J.*, 9:190–199 (1995).
Hodgson, *Exp. Opin. Ther. Pat.*, 5(5):459–468 (1995).
NIH, "Report and Recommendations . . . ", pp. 1–40 (Dec. 7, 1995).
Rojanasakul, *Adv. Drug Del. Rev.*, 18:115–131 (1996).
Fouts et al, *Vaccine*, 13(6):561–569 (1995).
Courvalin et al, *Comptes Rendus De L Academie Des Sciences: Serie II: Sciences De La Terre et Des Planetes*, 318(12):1207–1212 (1995).

*Primary Examiner*—Jasemine Chambers
*Assistant Examiner*—Jill D. Martin
*Attorney, Agent, or Firm*—Sughrue, Mion, Macpeak & Seas, PLLC

[57] ABSTRACT

A method for introducing and expressing genes in animal cells is disclosed comprising infecting said animal cells with live invasive bacteria, wherein said bacteria contain a eukaryotic expression cassette encoding said gene. The gene may encode, e.g., a vaccine antigen, an therapeutic agent, an immunoregulatory agent or a anti-sense RNA or a catalytic RNA.

15 Claims, 6 Drawing Sheets

METHOD FOR INTRODUCING AND EXPRESSING GENES IN ANIMAL CELLS, AND LIVE INVASIVE BACTERIAL VECTORS FOR USE IN THE SAME

This is a Continuation of application Ser. No. 08/433,790 filed May 3, 1998, (now U.S. Pat. No. 5,877,159) the disclosure of which is incorporated herein by reference.

The development of this invention was supported by the University of Maryland, Baltimore, Md.

The invention described herein was supported by funding from the National Institutes of Health (NIH 5-RO1-AI32879). The Government has certain rights.

FIELD OF THE INVENTION

The present invention relates to a method for introducing endogenous or foreign genes into animal cells using live invasive bacteria as vectors. The method allows for the delivery of eukaryotic expression cassettes encoding the endogenous or foreign genes into animal cells or animal tissue, and is useful for expressing, e.g., vaccine antigens, therapeutic agents, immunoregulatory agents, antisense RNAs, and catalytic RNAs, in animal cells or animal tissue.

BACKGROUND OF THE INVENTION

I. Live Bacterial Vector Vaccines

The advent of recombinant DNA technology has greatly accelerated the development of vaccines to control epidemic, endemic, and pandemic infectious diseases (Woodrow et al, *New Generation Vaccines: The Molecular Approach*, Eds., Marcel Dekker, Inc., New York, N.Y. (1989); Cryz, *Vaccines and Immunotherapy*, Ed., Pergamon Press, New York, N.Y. (1991); and Levine et al, *Ped. Ann.*, 22:719–725 (1993)). In particular, this technology has enabled the growth of a new class of vaccines called bacterial vector vaccines (Curtiss, In: *New Generation Vaccines: The Molecular Approach*, Ed., Marcel Dekker, Inc., New York, N.Y., pages 161–188 and 269–288 (1989); and Mims et al, In: *Medical Microbiology*, Eds., Mosby-Year Book Europe Ltd., London (1993)). These vaccines can enter the host, either orally, intranasally or parenterally. Once gaining access to the host, the bacterial vector vaccines express an engineered prokaryotic expression cassette contained therein that encodes a foreign antigen(s). Foreign antigens can be any protein (or part of a protein) or combination thereof from a bacterial, viral, or parasitic pathogen that has vaccine properties (*New Generation Vaccines: The Molecular Approach*, supra; Vaccines and Immunotherapy, supra; Hilleman, *Dev. Biol. Stand.*, 82:3–20 (1994);° Formal et al, *Infect. Immun.* 34:746–751 (1981); Gonzalez et al, *J. Infect. Dis.*, 169:927–931 (1994); Stevenson et al, *FEMS Lett.*, 28:317–320 (1985); Aggarwal et al, *J. Exp. Med.*, 172:1083–1090 (1990); Hone et al, *Microbial. Path.*, 5:407–418 (1988); Flynn et al, *Mol. Microbiol.*, 4:2111–2118 (1990); Walker et al, *Infect. Immun.*, 60:4260–4268 (1992); Cardenas et al, *Vacc.*, 11:126–135 (1993); Curtiss et al, *Dev. Biol. Stand.*, 82:23–33 (1994); Simonet et al, *Infect. Immun.*, 62:863–867 (1994); Charbit et al, *Vacc.*, 11:1221–1228 (1993); Turner et al, *Infect. Immun.*, 61:5374–5380 (1993); Schodel et al, *Infect. Immun.*, 62:1669–1676 (1994); Schodel et al, *J. Immunol.*, 145:4317–4321 (1990); Stabel et al, *Infect. Immun.*, 59:2941–2947 (1991); Brown, *J. Infect. Dis.*, 155:86–92 (1987); Doggett et al, *Infect. Immun.*, 61:1859–1866 (1993); Brett et al, *Immunol.*, 80:306–312 (1993); Yang et al, *J. Immunol.*, 145:2281–2285 (1990); Gao et al, *Infect. Immun.*, 60:3780–3789 (1992); and Chatfield et al, *Bio/Technology*, 10:888–892 (1992)). Delivery of the foreign antigen to the host tissue using bacterial vector vaccines results in host immune responses against the foreign antigen, which provide protection against the pathogen from which the foreign antigen originates (Mims, *The Pathogenesis of Infectious Disease*, Academic Press, London (1987); and *New Generation Vaccines: The Molecular Approach*, supra).

Of the bacterial vector vaccines, live oral Salmonella vector vaccines have been studied most extensively. There are numerous examples showing that Salmonella vectors are capable of eliciting humoral and cellular immunity against bacterial, viral and parasitic antigens (Formal et al, *Infect. Immun.*, 34:746–751 (1981); Gonzalez et al, supra; Stevenson et al, supra; Aggarwal et al, supra; Hone et al, supra; Flynn et al, supra; Walker et al, supra; Cardenas et al, supra; Curtiss et al, supra; Simonet et al, supra; Charbit et al, supra; Turner et al, supra; Schodel et al, supra, Schodel et al (1990), supra; Stabel et al, supra; Brown, supra; Doggett et al, supra; Brett et al, supra; Yang et al, supra; Gao et al, supra; and Chatfield et al, supra). These humoral responses occur in the mucosal (Stevenson et al, supra; Cardenas et al, supra; Walker et al, supra; and Simonet et al, supra), and systemic compartments (Gonzalez et al, supra; Stevenson et al, supra; Aggarwal et al, supra; Hone et al, supra; Flynn et al, supra; Walker et al, supra; Cardenas et al, supra; Curtiss et al, supra; Simonet et al, supra; Charbit et al, supra; Turner et al, supra; Schodel et al, supra, Schodel et al (1990), supra; Stabel et al, supra; Brown, supra; Doggett et al, supra; Brett et al, supra; Yang et al, supra; Gao et al, supra; and Chatfield et al, supra). Live oral Salmonella vector vaccines also elicit T cell responses against foreign antigens (Wick et al, *Infect. Immun.*, 62:4542–4548 (1994)). These include antigen-specific cytotoxic CD8[+] T cell responses (Gonzalez et al, supra; Aggarwal et al, supra; Flynn et al, supra; Turner et al, supra; and Gao et al, supra).

Ideally, bacterial vector vaccines are genetically defined, attenuated and well-tolerated by the recipient animal or human, and retain immunogenicity (Hone et al, *Vaccine*, 9:810–816 (1991); Tacket et al, *Infect. Immun.*, 60:536–541 (1992); Hone et al, *J. Clin. Invest.*, 90:412–420 (1992); Chatfield et al, *Vaccine*, 10:8–11 (1992); Tacket et al, *Vaccine*, 10:443–446 (1992); and Mims, supra). Recently, the number of potential bacterial vector vaccines for the delivery of prokaryotic expression cassettes has grown. They now include, but are not restricted to *Yersinia enterocolitica* (van Damme et al, *Gastroenterol.*, 103:520–531 (1992)), *Shigella* spp. (Noriega et al, *Infect. Immun.*, 62:5168–5172 (1994)), *Vibrio cholerae* (Levine et al, In: *Vibrio cholerae, Molecular to Global Perspectives*, Wachsmuth et al, Eds, ASM Press, Washington, D.C., pages 395–414 (1994)), *Mycobacterium* strain BCG (Lagranderie et al, *Vaccine*, 11:1283–1290 (1993); Flynn, *Cell. Molec. Biol.*, 40(Suppl. 1):31–36 (1994)), and *Listeria monocytogenes* (Schafer et al, *J. Immunol.*, 149:53–59 (1992)) vector vaccines.

II. Eukaryotic and Prokaryotic Expression Cassettes

Normally, an expression cassette is composed of a promoter region, a transcriptional initiation site, a ribosome binding site (RBS), an open reading frame (orf) encoding a protein (or fragment thereof), with or without sites for RNA splicing (only in eukaryotes), a translational stop codon, a transcriptional terminator and post-transcriptional polyadenosine processing sites (only in eukaryotes) (Wormington, *Curr. Opin. Cell Biol.*, 5:950–954 (1993); Reznikoff et al, *Maximizing Gene Expression*, Eds., Butterworths, Stoneham, Mass. (1986)). The promoter region, the RBS, the splicing sites, the transcriptional terminator and post-transcriptional poly-adenosine processing sites are markedly different in eukaryotic expression cassettes than those found in prokaryotic expression cassettes (Wasylyk, In: *Maximizing Gene Expression*, supra, pages 79–99; Reznikoff et al, In: *Maximizing Gene Expression*, supra, pages 1–34; and Lewin, Genes V, Oxford University Press, Oxford (1994)). These differences prevent expression of prokaryotic expression cassettes in eukaryotic cells and visa versa (Miller et al, *Mol. Micro.*, 4:881–893 (1990); and Williamson et al, *Appl. Env. Micro.*, 60:771–776 (1994)).

Prokaryotic promoters are not active in eukaryotic cells and eukaryotic promoters are not active in prokaryotic cells (Eick et al, *Trends in Genetics*, 10:292–296 (1994)). The basis for the functional diversity of eukaryotic versus prokaryotic promoters is mediated by RNA-polymerase, transcription regulatory factors and the DNA structure of the promoter (Eick et al, supra).

RNA polymerases are DNA-binding proteins that recognize specific sequences in the DNA of promoter regions. RNA polymerases catalyze the synthesis of RNA molecules by polymerizing nucleoside triphosphates in the specific order that is dictated by the DNA coding sequence (Libby et al, *Mol. Micro.*, 5:999–1004 (1991); Kerppola et al, *FASEB J.*, 5:2833–2842 (1991); Alberts et al, *Molecular Biology of the Cell*, Eds., Garland Publishing Inc, New York, N.Y. (1994); Watson et al, *Molecular Biology of the Gene*, Vol. 1, Eds., The Benjamin/Cummings Publishing Comp. Inc., Menlo Park Calif. (1987); and Lewin, supra). RNA polymerases of prokaryotes typically are composed of two identical α subunits and two similar, but non-identical, β and β' subunits (Ishihama, *Mol. Micro.*, 6:3283–3288 (1992); Watson et al, supra; Alberts et al, supra; and Lewin, supra). The specificity of prokaryotic RNA polymerases for a given promoter region is mediated by specific a factors that recognize core sequences encoded by the DNA in the promoter regions (Libby et al, supra; and Lewin, supra).

In eukaryotic cells, there are three RNA polymerases. Each of the different RNA polymerases contain 10 to 15 different subunits and each performs a different function (Kerppola et al, supra; Larson et al, *Biochem. Cell. Biol.*, 69:5–22 (1991); Archambault et al, *Microbiol. Rev.*, 57:703–724 (1993); Watson et al, supra; Alberts et al, supra; and Lewin, supra). In addition, specific DNA-binding factors may be required for the association of eukaryotic RNA polymerases to the DNA in a promoter region (Darnell et al, *Molecular Cell Biology*, Scientific American Books, Inc., W. H. Freeman and Co., New York, N.Y. (1990); Hori et al, *Curr. Opin. Gen. Devel.*, 4:236–244 (1994); Lewin, supra; Watson et al, supra; and Alberts et al, supra). These binding factors recognize specific sequences in the DNA, and also interact with the eukaryotic RNA polymerases.

There is little similarity between the primary DNA sequence of prokaryotic promoters and the primary DNA sequence of eukaryotic promoters. The DNA structure of prokaryotic promoters is relatively simple, consisting of −10 and −35 regions and proximal regulatory sequences (Darnell et al, supra; Lewin, supra; Watson et al, supra; and Alberts et al, supra) Prokaryotic promoters are located upstream of the transcription start site. Eukaryotic promoters, in contrast, are composed of a core unit, which is usually located from 50 bp upstream to 20 bp downstream of the transcriptional start site (Darnell et al, supra; Lewin, supra; Watson et al, supra; and Alberts et al, supra), and enhancer sequences that are located from about 100 to 200 bp upstream of the transcriptional start, but also can be located in distal locations (Sonenberg, *Curr. Opin. Gen. Devel.*, 4:310–315 (1994); Geballe et al, *Trends Bio. Sci.*, 1:159–164 (1994); and Lewin, supra).

The RBS is the site recognized by the ribosome for binding to the 5' end of messenger RNA (mRNA) molecules. This binding is essential for the translation of mRNA into a protein by the ribosome. In prokaryotes, the RBS in the 5' end of the mRNA molecule is a sequence that is complementary to the 3' end of the small ribosomal RNA molecule (5S rRNA) (Chatterji et al, *Ind. J. Biochem. Biophys.*, 29:128–134 (1992); and Darnell et al, supra; Lewin, supra; Watson et al, supra; and Watson et al, supra). The presence of the RBS promotes binding of the ribosome to the 5' end of the nascent mRNA molecule. Translation is then initiated at the first AUG codon encountered by the scanning ribosome (Darnell et al, supra; Lewin, supra; Watson et al, supra; and Alberts et al, supra). At present, no such recognition pattern has been observed in eukaryotic mRNA-ribosome interactions (Eick et al, supra). In addition, prior to initiation of translation of eukaryotic mRNA, the 5' end of the mRNA molecule is "capped" by addition of methylated guanylate to the first mRNA nucleotide residue (Darnell et al, supra; Lewin, supra; Watson et al, supra; and Alberts et al, supra). It has been proposed that recognition of the translational start site in mRNA by the eukaryotic ribosomes involves recognition of the cap, followed by binding to specific sequences surrounding the initiation codon on the mRNA. It is possible for cap independent translation initiation to occur and/or to place multiple eukaryotic coding sequences within a eukaryotic expression cassette if a cap-independent translation enhancer (CITE) sequence, such as derived from encephalomyocarditis virus (Duke et al, *J. Virol.*, 66:1602–1609 (1992)), is included prior to or between the coding regions. However, the initiating AUG codon is not necessarily the first AUG codon encountered by the ribosome (Louis et al, *Molec. Biol. Rep.*, 13:103–115 (1988); and Voorma et al, *Molec. Biol. Rep.*, 19:139–145 (1994); Lewin, supra; Watson et al, supra; and Alberts et al, supra). Thus, RBS binding sequences in eukaryotes are sufficiently divergent from that of prokaryotic RBS such that the two are not interchangeable.

Termination of transcription in prokaryotes is mediated by rho-independent and rho-dependent stem loops (Richardson, *Crit. Rev. Biochem. Mol. Biol.*, 28:1–30 (1993); Platt, *Molec. Microbiol.*, 11:983–990 (1994); and Lewin, supra). In contrast, terminator loops are not commonly found downstream of eukaryotic expression cassettes, and transcription often extends beyond the end of the open reading frame (Tuite et al, *Mol. Biol. Reps.*, 19:171–181 (1994)). However, usually the over-extended mRNA is specifically cleaved by endonucleases, and the 3' end of the mRNA is polyadenylated by poly-A polymerase (Proudfoot, *Cell*, 64:671–674 (1991); Wahle, *Bioassays*, 14:113–118 (1992); Lewin, supra; and Watson et al, supra). Sequences that are recognized by the endonucleases and poly-A polymerase must be included in the 3' end of the mRNA molecule for these post-translation modifications to occur. Polyadenylation of the 3' end of mRNA molecules is thought to be a necessary step prior to transport of mRNA to the cytoplasm of eukaryotic cells and translation into proteins (Sachs et al, *J. Biol. Chem.*, 268:22955–22958 (1993); and Sachs, *Cell*, 74:413–421 (1993)). A eukaryotic expression cassette does not need to code for a functional gene product, i.e., it may also code for a partial gene product which acts as an inhibitor of a eukaryotic enzyme (Warne et al, *Nature*, 364:352–355 (1993); and Wang, *J. Cell Biochem.*, 45:49–53 (1991)), an antisense RNA (Magrath, *Ann. Oncol.*, 5(Suppl 1):67–70 (1994); Milligan et al, *Ann. NY Acad. Sci.*, 716:228–241 (1994); and Schreier, *Pharma. Acta Helv.*, 68:145–159 (1994)), a catalytic RNA (Cech, *Biochem. Soc.*

Trans., 21:229–234 (1993); Cech, *Gene*, 135:33–36 (1993); Long et al, *FASE J.*, 7:25–30; and Rosi et al, *Pharm. Therap.*, 50:245–254 (1991)), or any other sequence which can be transcribed into RNA.

Due to a need for eukaryotic expression cassettes to study the biology of eukaryotic cells, a number of eukaryotic expression plasmids are now readily available. These include, but are not limited to, commercial products from companies, such as Invitrogen Corporation (San Diego, Calif.), Stratagene (La Jolla, Calif.), ClonTech (Palo Alto, Calif.) and Promega Corporation (Madison, Wis.). All of these plasmids contain the elements of a eukaryotic expression cassette listed above, and many also contain a prokaryotic promoter sequence such that the gene placed downstream from the promoter sequences will be expressed in a prokaryotic as well as in an eukaryotic cell, e.g., plasmid pSVβ-gal contains the eukaryotic SV40 promoter and the prokaryotic gpt promoter which allows for the expression of the β-galactosidase gene in either prokaryotic cells or eukaryotic cells (Promega Corp.).

III. Delivery of Eukaryotic Expression Cassettes to Plant Cells

The use of *Agrobacterium tumerfacium* Ti plasmid to stably deliver DNA to plant cells has been a fundamental component of the boom in plant biotechnology. This system is unique in that it uses a pilus-like structure which binds to the plant cell via specific receptors, and then through a process that resembles bacterial conjugation, delivers the Ti plasmid-linked DNA to the plant cell (Zambryski, *Ann. Rev. Genet.*, 22:1–30 (1988); Lessl et al, *Cell*, 77:321–324 (1994); and Walden et al, *Eur. J. Biochem.*, 192:563–576 (1990)). The specificity of this delivery system for plants, however, renders it ineffective for delivery of DNA to animal cells (Chilton, *Proc. Natl. Acad. Sci., USA*, 90:3119–3120 (1993); and Walden et al, supra).

IV. Delivery of Eukaryotic Expression Cassettes to Animal Cells

There are several techniques for introducing DNA into animal cells cultured in vitro. These include chemical methods (Felgner et al, *Proc. Natl. Acad. Sci., USA*, 84:7413–7417 (1987); Bothwell et al, *Methods for Cloning and Analysis of Eukaryotic Genes*, Eds., Jones and Bartlett Publishers Inc., Boston, Mass. (1990), Ausubel et al, *Short Protocols in Molecular Biology*, John Wiley and Sons, New York, N.Y. (1992); and Farhood, *Annal. N.Y. Acad. Sci.*, 716:23–34 (1994)), use of protoplasts (Bothwell, supra) or electrical pulses (Vatteroni et al, *Mutn. Res.*, 291:163–169 (1993); Sabelnikov, *Prog. Biophys. Mol. Biol.*, 62:119–152 (1994); Brothwell et al, supra; and Ausubel et al, supra), use of attenuated viruses (Moss, *Dev. Biol. Stan.*, 82:55–63 (1994); and Brothwell et al, supra), as well as physical methods (Fynan et al, supra; Johnston et al, *Meth. Cell Biol*, 43(Pt A):353–365 (1994); Brothwell et al, supra; and Ausubel et al, supra).

Successful delivery of DNA to animal tissue has been achieved by cationic liposomes (Watanabe et al, *Mol. Reprod. Dev.*, 38:268–274 (1994)), direct injection of naked DNA into animal muscle tissue (Robinson et al, *Vacc.*, 11:957–960 (1993); Hoffman et al, *Vacc.*, 12:1529–1533; (1994); Xiang et al, *Virol.*, 199:132–140 (1994); Webster et al, *Vacc.*, 12:1495–1498 (1994); Davis et al, *Vacc.*, 12:1503–1509 (1994); and Davis et al, *Hum. Molec. Gen.*, 2:1847–1851 (1993)), and embryos (Naito et al, *Mol. Reprod. Dev.*, 39:153–161 (1994); and Burdon et al, *Mol. Reprod. Dev.*, 33:436–442 (1992)), or intradermal injection of DNA using "gene gun" technology (Johnston et al, supra). A limitation of these techniques is that they only efficiently deliver DNA to parenteral sites. At present, effective delivery of eukaryotic expression cassettes to mucosal tissue has been met with limited success. This is presumably due to poor access to these sites, toxicity of the delivery vehicles or instability of the delivery vehicles when delivered orally.

The commercial application of DNA delivery technology to animal cells is broad and includes delivery of vaccine antigens (Fynan et al, *Proc. Natl. Acad. Sci., USA*, 90:11478–11482 (1993)), immunotherapeutic agents, and gene therapeutic agents (Darris et al, *Cancer*, 74(3 Suppl.):1021–1025 (1994); Magrath, *Ann. Oncol.*, 5(Suppl 1):67–70 (1994); Milligan et al, *Ann. NY Acad. Sci.*, 716:228–241 (1994); Schreier, *Pharma. Acta Helv.*, 68:145–159 (1994); Cech, *Biochem. Soc. Trans.*, 21:229–234 (1993); Cech, *Gene*, 135:33–36 (1993); Long et al, *FASEB J.*, 7:25–30 (1993); and Rosi et al, *Pharm. Therap.*, 50:245–254 1991)).

The delivery of endogenous and foreign genes to animal tissue for gene therapy has shown significant promise in experimental animals and volunteers (Nabel, *Circulation*, 91:541–548 (1995); Coovert et al, *Curr. Opin. Neuro.*, 7:463–470 (1994); Foa, *Bill. Clin. Haemat.*, 7:421–434 (1994); Bowers et al, *J. Am. Diet. Assoc.*, 95:53–59 (1995); Perales et al, *Eur. J. Biochem.*, 226:255–266 (1994); Danko et al, *Vacc.*, 12:1499–1502 (1994); Conry et al, *Canc. Res.*, 54:1164–1168 (1994); and Smith, *J. Hemat.*, 1:155–166 (1992)). Recently, naked DNA vaccines carrying eukaryotic expression cassettes have been used to successfully immunize against influenza both in chickens (Robinson et al, supra) and ferrets (Webster et al, *Vacc.*, 12:1495–1498 (1994)); against *Plasmodium yoelii* in mice (Hoffman et al, supra); against rabies in mice (Xiang et al, supra); against human carcinoembryonic antigen in mice (Conry et al, supra) and against hepatitis B in mice (Davis et al, supra). These observations open the additional possibility that delivery of endogenous and foreign genes to animal tissue could be used for prophylactic and therapeutic applications.

Therefore, there is a need to deliver eukaryotic expression cassettes, encoding endogenous or foreign genes that are vaccines or therapeutic agents to animal cells or tissue. In particular, a method that delivers eukaryotic expression cassettes to mucosal surfaces is highly desirable. Bacterial vector vaccines have been used in the past to deliver foreign antigens encoded on prokaryotic expression cassettes to animal tissue at mucosal sites.

The present invention describes a novel and unexpected finding that invasive bacteria are capable of delivering eukaryotic expression cassettes to animal cells and tissue. An important aspect of using live invasive bacteria to deliver eukaryotic expression cassettes is that they are capable of delivering DNA to mucosal sites.

Heretofore, there has been no documented demonstration of live bacteria invading animal cells and introducing a eukaryotic expression cassette(s), which then is expressed by the infected cells and progeny thereof. That is, the present invention provides the first documentation of genetic exchange between live invasive bacteria and animals cells. Heretofore, foreign antigen delivery by live bacterial vector vaccines merely involved delivery of prokaryotic expression cassettes to and expression of the foreign antigen by the bacterial vaccine vector, in animal cells or tissues. In contrast, the present invention involves the delivery of eukaryotic expression cassettes by live bacterial strains to animal cells in vitro or to cells in animal tissue, and expression of the eukaryotic expression cassettes by the animal cell or cells in animal tissue.

SUMMARY OF THE INVENTION

An object of the present invention is to use live invasive bacteria to deliver one or more eukaryotic expression cassettes to animal cells or animal tissue.

Another object of the present invention is to use live invasive bacteria to deliver one or more eukaryotic expression cassettes encoding a vaccine antigen(s) to animal cells or animal tissue.

Another object of the present invention is to use live invasive bacteria to deliver one or more eukaryotic expression cassettes encoding therapeutic agents to animal cells or animal tissue.

Yet another objective of the present invention is to use live invasive bacteria to deliver one or more eukaryotic expression cassettes encoding biologically active RNA species to animal cells or animal tissue.

These and other objects of the present invention, which will be apparent from the detailed description of the invention provided hereinafter, have been met in one embodiment by a method for introducing and expressing a gene in animal cells comprising infecting said animal cells with live invasive bacteria, wherein said bacteria contain a eukaryotic expression cassette encoding said gene.

In another embodiment, the present invention relates to live invasive bacteria which contain one or more eukaryotic expression cassettes encoding an endogenous or foreign gene.

DETAILED DESCRIPTION OF THE INVENTION

As discussed above, in one embodiment, the present invention relates to a method for introducing and expressing a gene in animal cells comprising infecting said animal cells with live invasive bacteria, wherein said bacteria contain a eukaryotic expression cassette encoding said gene.

Animal cells are defined as nucleated, non-chloroplast containing cells derived from or present in multicellular organisms whose taxanomic position lies within the kingdom animalia. The cells may be present in the intact animal, a primary cell culture, explant culture or a transformed cell line. The particular tissue source of the cells is not critical to the present invention.

The recipient animal cells employed in the present invention are not critical thereto and include cells present in or derived from all organisms within the kingdom animalia, such as those of the families mammalia, pisces, avian, reptilia.

Preferred animal cells are mammalian cells, such as humans, bovine, ovine, porcine, feline, buffalo, canine, goat, equine, donkey, deer, and primate cells. The most preferred animal cells are human cells.

Examples of human cell lines include but are not limited to ATCC Nos. CCL 62, CCL 159, HTB 151, HTB 22, CCL 2, CRL 1634, CRL 8155, HTB 61, and HTB104.

Examples of bovine cell lines include ATCC Nos. CRL 6021, CRL 1733, CRL 6033, CRL 6023, CCL 44 and CRL 1390.

Examples of ovine cells lines include ATCC Nos. CRL 6540, CRL 6538, CRL 6548 and CRL 6546.

Examples of porcine cell lines include ATCC Nos. CL 184, CRL 6492, and CRL 1746.

Examples of feline cell lines include CRL 6077, CRL 6113, CRL 6140, CRL 6164, CCL 94, CCL 150, CRL 6075 and CRL 6123.

Examples of buffalo cell lines include CCL 40 and CRL 6072.

Examples of canine cells include ATCC Nos. CRL 6213, CCL 34, CRL 6202, CRL 6225, CRL 6215, CRL 6203 and CRL 6575.

Examples of goat derived cell lines include ATCC No. CCL 73 and ATCC No. CRL 6270.

Examples of horse derived cell lines include ATCC Nos. CCL 57 and CRL 6583.

Examples of deer cell lines include ATCC Nos. CRL 6193–6196.

Examples of primate derived cell lines include those from chimpanzee's such as ATCC Nos. CRL 6312, CRL 6304, and CRL 1868; monkey cell lines such as ATCC Nos. CRL 1576, CCL 26, and CCL 161; orangautan cell line ATCC No. CRL 1850; and gorilla cell line ATCC No. CRL 1854.

As used herein, "invasive bacteria" are bacteria that are capable of delivering eukaryotic expression cassettes to animal cells or animal tissue. "Invasive bacteria" include bacteria that are naturally capable of entering the cytoplasm or nucleus of animal cells, as well as bacteria that are genetically engineered to enter the cytoplasm or nucleus of animal cells or cells in animal tissue.

The particular naturally occurring invasive bacteria employed in the present invention is not critical thereto. Examples of such naturally-occurring invasive bacteria include, but are not limited to, Shigella spp, Listeria spp., Rickettsia spp and enteroinvasive Escherichia coli.

The particular Shigella strain employed is not critical to the present invention. Examples of Shigella strains which can be employed in the present invention include Shigella flexneri 2a (ATCC No. 29903), Shigella sonnei (ATCC No. 29930), and Shigella disenteriae (ATCC No. 13313). An attenuated Shigella strain, such as Shigella flexneri 2a 2457T ΔaroAΔvirG mutant CVD 1203 (Noriega et al, supra), Shigella flexneri M90T ΔicsA mutant (Goldberg et al, Infect. Immun., 62:5664–5668 (1994)), Shigella flexneri Y SFL114 aroD mutant (Karnell et al, Vacc., 10:167–174 (1992)), and Shigella flexneri ΔaroAΔaroD mutant (Verma et al, Vacc., 9:6–9 (1991)) are preferably employed in the present invention. Alternatively, new attenuated Shigella spp. strains can be constructed by introducing an attenuating mutation either singularly or in conjunction with one or more additional attenuating mutations.

Attenuating mutations can be introduced into bacterial pathogens using non-specific mutagenesis either chemically, using agents such as N-methyl-N'-nitro-N-nitrosoguanidine, or using recombinant DNA techniques; classic genetic techniques, such as Tn10 mutagenesis, P22-mediated transduction, λ phage mediated crossover, and conjugational transfer; or site-directed mutagenesis using recombinant DNA techniques. Recombinant DNA techniques are preferable since strains constructed by recombinant DNA techniques are far more defined. Examples of such attenuating mutations include, but are not limited to:

(i). auxotrophic mutations, such as aro (Hoiseth et al, *Nature*, 291:238–239 (1981)), qua (McFarland et al, *Microbiol. Path.*, 3:129–141 (1987)), nad (Park et al, *J. Bact.*, 170:3725–3730 (1 9 8 8), thy (Nnalue et al, *Infect. Immun.*, 55:955–962 (1987)), and asd (Curtiss, supra) mutations;

(ii) mutations that inactivate global regulatory functions, such as cya (Curtiss et al, *Infect. Immun.*, 55:3035–3043 (1987) ), crp (Curtiss et al (1987), supra), phoP/phoQ (Groisman et al, *Proc. Natl. Acad. Sci., USA*, 86:7077–7081 (1989); and Miller et al, *Proc. Natl. Acad. Sci., USA*, 86:5054–5058 (1989)), phoP$^c$ (Miller et al, *J. Bact.*, 172:2485–2490 (1990)) or ompR (Dorman et al, *Infect. Immun.*, 57:2136–2140 (1989)) mutations;

(iii) mutations that modify the stress response, such as recA (Buchmeier et al, *Mol. Micro.*, 7:933–936 (1993)), htrA (Johnson et al, *Mol. Micro.*, 5:401–407 (1991)), htpR (Neidhardt et al, *Biochem. Biophys. Res. Com.*, 100:894–900 (1981)), hsp (Neidhardt et al, *Ann. Rev. Genet.*, 18:295–329 (1984)) and groEL (Buchmeier et al, *Sci.*, 248:730–732 (1990)) mutations;

(iv) mutations in specific virulence factors, such as lsyA (Libby et al, *Proc. Natl. Acad. Sci., USA*, 91:489–493 (1994)), pag or prg (Miller et al (1990), supra; and Miller et al (1989), supra), iscA or virG (d'Hauteville et al, *Mol. Micro.*, 6:833–841 (1992)), plcA (Mengaud et al, *Mol. Microbiol.*, 5:367–72 (1991); Camilli et al, *J. Exp. Med*, 173:751–754 (1991)), and act (Brundage et al, *Proc. Natl. Acad. Sci., USA*, 90:11890–11894 (1993)) mutations;

(v) mutations that affect DNA topology, such as topA (Galan et al, *Infect. Immun.*, 58:1879–1885 (1990)) mutation;

(vi) mutations that block biogenesis of surface polysaccharides, such as rfb, galE (Hone et al, *J. Infect. Dis.*, 156:164–167 (1987)) or via (Popoff et al, *J. Gen. Microbiol.*, 138:297–304 (1992)) mutations;

(vii) mutations that modify suicide systems, such as sacB (Recorbet et al, *App. Environ. Micro.*, 59:1361–1366 (1993); Quandt et al, *Gene*, 127:15–21 (1993)), nuc (Ahrenholtz et al, *App. Environ. Micro.*, 60:3746–3751 (1994)), hok, gef, kil, or phlA (Molin et al, *Ann. Rev. Microbiol.*, 47:139–166 (1993)) mutations;

(viii) mutations that introduce suicide systems, such as lysogens encoded by P22 (Rennell et al, *Virol.*, 143:280–289 (1985)), λ murein transglycosylase (Bienkowska-Szewczyk et al, *Mol. Gen. Genet.*, 184:111–114 (1981)) or S-gene (Reader et al, *Virol.*, 43:623–628 (1971)); and (ix) mutations that disrupt or modify the correct cell cycle, such as minB (de Boer et al, *Cell*, 56:641–649 (1989)) mutation.

The attenuating mutations can be either constitutively expressed or under the control of inducible promoters, such as the temperature sensitive heat shock family of promoters (Neidhardt et al, supra), or the anaerobically induced nirB promoter (Harborne et al, *Mol. Micro.*, 6:2805–2813 (1992)) or repressible promoters, such as uapA (Gorfinkiel et al, *J. Biol. Chem.*, 268:23376–23381 (1993)) or gcv (Stauffer et al, *J. Bact.*, 176:6159–6164 (1994)).

The particular Listeria strain employed is not critical to the present invention. Examples of Listeria strains which can be employed in the present invention include *Listeria monocytogenes* (ATCC No. 15313). Attenuated Listeria strains, such as *L. monocytogenes* ΔactA mutant (Brundage et al, supra) or *L. monocytogenes* ΔplcA (Camilli et al, *J. Exp. Med.*, 173:751–754 (1991)) are preferably used in the present invention. Alternatively, new attenuated Listeria strains can be constructed by introducing one or more attenuating mutations as described for Shigella spp. above.

The particular Rickettsia strain employed is not critical to the present invention. Examples of Rickettsia strains which can be employed in the present invention include *Rickettsia rickettsiae* (ATCC Nos. VR149 and VR891), *Rickettsia prowaseckii* (ATCC No. VR233.), *Rickettsia tsutsugamuchi* (ATCC Nos. VR312, VR150 and VR609), *Rickettsia mooseri* (ATCC No. VR144), *Rickettsia sibirica* (ATCC No. VR151), and *Rochalimaea quitana* (ATCC No. VR358). Attenuated Rickettsia strains are preferably used in the present invention and can be constructed by introducing one or more attenuating mutations as described for Shigella spp. above.

The particular enteroinvasive Escherichia strain employed is not critical to the present invention.

Examples of enteroinvasive Escherichia strains which can be employed in the present invention include *Escherichia coli* strains 4608–58, 1184–68, 53638-C-17, 13–80, and 6–81 (Sansonetti et al, *Ann. Microbiol. (Inst. Pasteur)*, 132A:351–355 (1982)). Attenuated enteroinvasive Escherichia strains are preferably used in the present invention and can be constructed by introducing one or more attenuating mutations as described for Shigella spp. above.

Examples of bacteria which can be genetically engineered to be invasive include, but are not limited to, Yersinia spp., Escherichia spp., Klebsiella spp., Bordetella spp., Neisseria spp., Aeromonas spp., Franciesella spp., Corynebacterium spp., Citrobacter spp., Chlamydia spp., Hemophilus spp., Brucella spp., Mycobacterium spp., Legionella spp., Rhodococcus spp., Pseudomonas spp., Helicobacter spp., Salmonella spp., Vibrio spp., Bacillus spp., and Erysipelothrix spp. These organisms can be engineered to mimic the invasion properties of Shigella spp., Listeria spp., Rickettsia spp., or enteroinvasive *E. coli* spp. by inserting genes that enable them to access the cytoplasm of an animal cell.

Examples of such genes include the invasive proteins of Shigella, hemolysin or the invasion plasmid of Escherichia, or listeriolysin O of Listeria, as such techniques are known to result in strains that are capable of entering the cytoplasm of infected animal cells (Formal et al, *Infect. Immun.*, 46:465 (i984); Bielecke et al, *Nature*, 345:175–176 (1990); Small et al, In: *Microbiology*-1986, pages 121–124, Levine et al, Eds., American Society for Microbiology, Washington, D.C. (1986); and Zychlinsky et al, *Molec. Micro.*, 11:619–627 (1994)). Any gene or combination of genes, from one or more sources, that mediates entry into the cytoplasm of animal cells will suffice. Thus, such genes are not limited to bacterial genes, and include viral genes, such as influenza virus hemagglutinin HA-2 which promotes endosmolysis (Plank et al, *J. Biol. Chem.*, 269:12918–12924 (1994)).

The above invasive genes can be introduced into the target strain using chromosome or plasmid mobilization (Miller, *A Short Course in Bacterial Genetics*, Cold Spring Harbor Laboratory Press, Cold Spring Harbor, N.Y. (1992); Bothwell et al, supra; and Ausubel et al, supra), bacteriophage-mediated transduction (de Boer, supra; Miller, supra; and 
Ausubel et al, supra), or chemical (Bothwell et al, supra; Ausubel et al, supra; Felgner et al, supra; and Farhood, supra), electroporation (Bothwel et al, supra; Ausubel et al, supra; and Sambrook, *Molecular Cloning: A Laboratory Manual*, Cold Spring Harbor Laboratory Press, Cold Spring Harbor, N.Y.) and physical transformation techniques (Johnston et al, supra; and Bothwell, supra). The genes can be incorporated on bacteriophage (de Boer et al, *Cell*, 56:641–649 (1989)), plasmids vectors (Curtiss et al, supra) or spliced into the chromosome (Hone et al, supra) of the target strain.

The particular Yersinia strain employed is not critical to the present invention. Examples of Yersinia strains which can be employed in the present invention include *Y. enterocolitica* (ATCC No. 9610) or *Y. pestis* (ATCC No. 19428). Attenuated Yerinia strains, such as *Y. enterocolitica* Ye03-R2 (al-Hendy et al, *Infect. Immun.*, 60:870–875 (1992)) or *Y. enterocolitica* aroA (O'Gaora et al, *Micro. Path.*, 9:105–116. (1990)) are preferably used in the present invention. Alternatively, new attenuated Yersinia strains can be constructed by introducing one or more attenuating mutations as described for Shigella spp. above.

The particular Escherichia strain employed is not critical to the present invention. Examples of Escherichia strains which can be employed in the present invention include *E. coli* H10407 (Elinghorst et al, *Infect. Immun.*, 60:2409–2417 (1992)), and *E. coli* EFC4, CFT325 and CPZ005 (Donnenberg et al, *J. Infect. Dis.*, 169:831–838 (1994)). Attenuated Escherichia strains, such as the attenuated turkey pathogen *E. coli* 02 carAB mutant (Kwaga et al, *Infect. Immun.*, 62:3766–3772 (1994) ) are preferably used in the present invention. Alternatively, new attenuated Escherichia strains can be constructed by introducing one or more attenuating mutations as described for Shigella spp. above.

The particular Klebsiella strain employed is not critical to the present invention. Examples of Klebsiella strains which can be employed in the present invention include *K. pneuoniae* (ATCC No. 13884). Attenuated Klebsiella strains are preferably used in the present invention, and can be constructed by introducing one or more attenuating mutations as described for Shigella spp. above.

The particular Bordetella strain employed is not critical to the present invention. Examples of Bordetella strains which can be employed in the present invention include *B. bronchiseptica* (ATCC No. 19395). Attenuated Bordetella strains are preferably used in the present invention, and can be constructed by introducing one or more attenuating mutations as described for Shigella spp. above.

The particular Neisseria strain employed is not critical to the present invention. Examples of Neisseria strains which can be employed in the present invention include *N. meningitidis* (ATCC No. 13077) and *N. gonorrhoeae* (ATCC No. 19424). Attenuated Neisseria strains, such as *N. gonorrhoeae* MS11 aro mutant (Chamberlain et al, *Micro. Path.*, 15:51–63 (1993)) are preferably used in the present invention. Alternatively, new attenuated Neisseria strains can be constructed by introducing one or more attenuating mutations as described for Shigella spp. above.

The particular Aeromonas strain employed is not critical to the present invention. Examples of Aeromonas strains which can be employed in the present invention include *A. eucrenophila* (ATCC No. 23309). Alternatively, new attenuated Aeromonas strains can be constructed by introducing one or more attenuating mutations as described for Shigella spp. above.

The particular Franciesella strain employed is not critical to the present invention. Examples of Franiesella strains which can be employed in the present invention include *F. tularensis* (ATCC No. 15482). Attenuated Franciesella strains are preferably used in the present invention, and can be constructed by introducing one or more attenuating mutations as described for Shigella spp. above.

The particular Corynebacterium strain employed is not critical to the present invention. Examples of Corynebacterium strains which can be employed in the present invention include *C. pseudotuberculosis* (ATCC No. 19410). Attenuated Corynebacterium strains are preferably used in the present invention, and can be constructed by introducing one or more attenuating mutations as described for Shigella spp. above.

The particular Citrobacter strain employed is not critical to the present invention. Examples of Citrobacter strains which can be employed in the present invention include *C. freundii* (ATCC No. 8090). Attenuated Citrobacter strains are preferably used in the present invention, and can be constructed by introducing one or more attenuating mutations as described for Shigella spp. above.

The particular Chlamydia strain employed is not critical to the present invention. Examples of Chlamydia strains which can be employed in the present invention include *C. pneumoniae* (ATCC No. VR1310). Attenuated Chlamydia strains are preferably used in the present invention, and can be constructed by introducing one or more attenuating mutations as described for Shigella spp. above.

The particular Hemophilus strain employed is not critical to the present invention. Examples of Hemophilus strains which can be employed in the present invention include *H. sornnus* (ATCC No. 43625). Attenuated Hemophilus strains are preferably used in the present invention, and can be constructed by introducing one or more attenuating mutations as described for Shigella spp. above.

The particular Brucella strain employed is not critical to the present invention. Examples of Brucella strains which can be employed in the present invention include *B. abortus* (ATCC No. 23448). Attenuated Brucella strains are preferably used in the present invention, and can be constructed by introducing one or more attenuating mutations as described for Shigella spp. above.

The particular Mycobacterium strain employed is not critical to the present invention. Examples of Mycobacterium strains which can be employed in the present invention include *M. intracellulare* (ATCC No. 13950) and *M. tuberculosis* (ATCC No. 27294). Attenuated Mycobacterium strains are preferably used in the present invention, and can be constructed by introducing one or more attenuating mutations as described for Shigella spp. above.

The particular Legionella strain employed is not critical to the present invention. Examples of Legionella strains which can be employed in the present invention include *L. pneumophila* (ATCC No. 33156). Attenuated Legionella strains, such as a *L. pneumophila* mip mutant (Ott, *FEMS Micro. Rev.*, 14:161–176 (1994)) are preferably used in the present invention. Alternatively, new attenuated Legionella strains can be constructed by introducing one or more attenuating mutations as described for Shigella spp. above.

The particular Rhodococcus strain employed is not critical to the present invention. Examples of Rhodococcus strains which can be employed in the present invention include *R. equi* (ATCC No. 6939). Attenuated Rhodococcus strains are preferably used in the present invention, and can be constructed by introducing one or more attenuating mutations as described for Shigella spp. above.

The particular Pseudomonas strain employed is not critical to the present invention. Examples of Pseudomonas strains which can be employed in the present invention include *P. aeruginosa* (ATCC No. 23267). Attenuated Pseudomonas strains are preferably used in the present invention, and can be constructed by introducing one or more attenuating mutations as described for Shigella spp. above.

The particular Helicobacter strain employed is not critical to the present invention. Examples of Helicobacter strains which can be employed in the present invention include *H. mustelae* (ATCC No. 43772). Attenuated Helicobacter strains are preferably used in the present invention, and can be constructed by introducing one or more attenuating mutations as described for Shigella spp. above.

The particular Salmonella strain employed is not critical to the present invention. Examples of Salmonella strains which can be employed in the present invention include *Salmonella typhi* (ATCC No. 7251) and *S. typhimurium* (ATCC No. 13311). Attenuated Salmonella strains are preferably used in the present invention and include *S. typhi* aroAaroD (Hone et al, *Vacc.*, 9:810–816 (1991)) and *S. typhimurium* aroA mutant (Mastroeni et al, *Micro. Pathol.*, 13:477–491 (1992))). Alteratively, new attenuated Salmonella strains can be constructed by introducing one or more attenuating mutations as described for Shigella spp. above.

The particular Vibrio strain employed is not critical to the present invention. Examples of Vibrio strains which can be employed in the present invention include *Vibrio cholerae* (ATCC No. 14035) and *Vibrio cincinnatiensis* (ATCC No. 35912). Attenuated Vibrio strains are preferably used in the present invention and include *V. cholerae* RSI virulance mutant (Taylor et al, *J. Infect. Dis.*, 170:1518–1523 (1994)) and *V. cholerae* ctxA, ace, zot, cep mutant (Waldor et al, *J. Infect. Dis.*, 170:278–283 (1994)). Alternatively, new attenuated Vibrio strains can be constructed by introducing one or more attenuating mutations as described for Shigella spp. above.

The particular Bacillus strain employed is not critical to the present invention. Examples of Bacillus strains which can be employed in the present invention include *Bacillus subtilis* (ATCC No. 6051). Attenuated Bacillus strains are preferably used in the present invention and include *B. anthracis* mutant pX01 (Welkos et al, *Micro. Pathol.*, 14:381–388 (1993)) and attenuated BCG strains (Stover et al, *Nat.*, 351:456–460 (1991)). Alternatively, new attenuated Bacillus strains can be constructed by introducing one or more attenuating mutations as described for Shigella spp. above.

The particular Erysipelothrix strain employed is not critical to the present invention. Examples of Erysipelothrix strains which can be employed in the present invention include *Erysipelothrix rhusiopathiae* (ATCC No. 19414) and *Erysipelothrix tonsillarum* (ATCC No. 43339). Attenuated Erysipelothrix strains are preferably used in the present invention and include *E. rhusiopathiae* Kg-1a and Kg-2 (Watarai et al, *J. Vet. Med. Sci.*, 55:595–600 (1993)) and *E. rhusiopathiae* ORVAC mutant (Markowska-Daniel et al, *Int. J. Med. Microb. Virol. Parisit. Infect. Dis.*, 277:547–553 (1992)). Alternatively, new attenuated Erysipelothrix strains can be constructed by introducing one or more attenuating mutations as described for Shigella spp. above.

As discussed above, the recipient animal cells to which bacteria deliver a eukaryotic expression cassette may be those derived from fish, birds or reptiles.

Examples of bacteria which can naturally access the cytoplasm of fish cells include, but are not limited to *Aeromonas salminocida* (ATCC No. 33658) and *Aeromonas schuberii* (ATCC No. 43700). Attenuated bacteria are preferably used in the invention, and include *A. salmonicidia* vapA (Gustafson et al, *J. Mol. Biol.*, 237:452–463 (1994)) or *A. salmonicidia* aromatic-dependent mutant (Vaughan et al, *Infect. Immun.*, 61:2172–2181 (1993)).

Examples of bacteria which can naturally access the cytoplasm of avian cells include, but are not restricted to, *Salmonella galinarum* (ATCC No. 9184), *Salmonella enteriditis* (ATCC No. 4931) and *Salmonella typhimurium* (ATCC No. 6994). Attenuated bacteria are preferred to the invention and include attenuated Salmonella strains such as *S. galinarum* cya crp mutant (Curtiss et al, (1987) supra) or *S. enteritidis* aroA aromatic-dependent mutant CVL30 (Cooper et al, *Infect. Immun.*, 62:4739–4746 (1994)).

Examples of bacteria which can naturally access the cytoplasm of reptilian cells include, but are not restricted to, *Salmonella typhimurium* (ATCC No. 6994). Attenuated bacteria are preferable to the invention and include, attenuated strains such as *S. typhimuirum* aromatic-dependent mutant (Hormaeche et al, supra).

Again, the particular animal cells infected with the invasive bacteria are not critical to the present invention, and will depend on the host range of the invasive bacteria employed.

For example, Shigella flexneri infects human and primate cells, but rarely infects dogs and other animals (Kreig et al, Bergey's Manual of Systematic Bacteriology, Eds., Wilkins and Williams, Baltimore, Md. (1984)), while *Aeromonas salminocida* infects salmonid cells (Austin et al, *Bacterial Fish Pathogens: Diseases in Farmed and Wild Fishes*, Eds., Ellis Harwood Ltd., London (1987)).

The mucosal and systemic immune systems are compartmentalized (Mesteky, *J. Clin. Immunol.*, 7:265–270 (19870; Newby, In: *Local Immune Response of the Gut*, Boca Raton, CRC Press, Newby and Stocks Eds., pages 143–160 (1984); and Pascual et al., *Immuno. Methods.*, 5:56–72 (1994)). Thus, antigens delivered to mucosal surfaces elicit mucosal and systemic responses, whereas parentally delivered antigens elicit mainly systemic responses but only stimulate poor mucosal responses (Mesteky, supra). Moreover, mucosal stimulation at one mucosal site (for example the intestine) can result in development of immunity at other mucosal surfaces (for example genital/urinary tract) (Mesteky, supra). This phenomenon is referred to as the common mucosal system and is well documented (Mesteky, supra; and Pascual et al, supra).

The development of mucosal vaccines has been hindered by the poor immunogenicity of antigens when delivered by these routes. In this context, antigens can be divided into two classes: those that bind to intestinal surfaces and those that do not bind, where the former are significantly more immunogenic than the latter (De Aizpurua et al, *J. Exp. Med.*, 176:440–451 (1988)). Similarly, delivery of DNA molecules to mucosal surfaces is inefficient due to the many natural host defenses found at these surfaces, such as the gastric barrier and nucleases in the gastrointestinal tract, and the thick mucous layer in the respiratory tract.

One approach to circumvent these natural barrier functions of the host and enable access to mucosal compartment is to use bacterial vectors (Curtiss, In: *New Generation Vaccines: The Molecular Approach*, Ed., Marcel Dekker, Inc., New York, N.Y., pages 161–188 and 269–288 (1989); and Mims et al, In: *Medical Microbiology*, Eds., Mosby-Year Book Europe Ltd., London (1993)). Certain enteric and respiratory pathogens, for example, *E. coli*, Shigella, Listeria, Bordetella and Salmonella, are naturally adapted for this application, as these organisms possess the ability to attach to and invade host mucosal surfaces (Kreig et al, Supra). Therefore, in the present invention, live oral bacterial vectors can be engineered to deliver eukaryotic expression cassettes to the host mucosal compartment.

Alternatively, any bacteria could be genetically engineered to mimic mucosal tissue tropism and invasive properties, as discussed above, that thereby allow said bacteria to invade mucosal tissue, and deliver genes at those sites.

It is also possible to change the tissue specificity of the invasive bacteria by expression of a gene product singularly or in combination, e.g., the Plasmodium vivax reticulocyte binding proteins-1 and -2 bind specifically to erythrocytes in humans and primates (Galinski et al, *Cell*, 69:1213–1226 (1992)); Yersinia Invasin recognizes β1 integrin receptors (Isberg et al, *Trends Microbiol.*, 2:10–14 (1994)); asialoorosomucoid is a ligand for the asilogycoprotein receptor on hepatocytes (Wu et al, *J. Biol. Chem.*, 263:14621–14624 (1988)); presence of insulin-poly-L-lysine has been shown to target plasmid uptake to cells with an insulin receptor (Rosenkranz et al, *Expt. Cell Res.*, 199:323–329 (1992)); p60 of Listeria monocytogenes allows for tropism for hepatocytes (Hess et al, *Infect. Immun.*, 63:2047–2053 (1995)) and *Trypanosoma cruzi* expresses a 60 kDa surface protein which causes specific binding to the mammalian extracellular matrix by binding to heparin, heparin sulfate and collagen (Ortega-Barria et al, *Cell*, 67:411–421 (1991)).

The particular eukaryotic cassette employed in the present invention is not critical thereto, and can be selected from, e.g., any of the many commercially available cassettes, such as pCEP4 or pRc/RSV obtained from Invitrogen Corporation (San Diego, Calif.), pXT1, pSG5, pPbac or pMbac obtained from Stratagene (La Jolla, Calif.), pPUR or pMAM obtained from ClonTech (Palo Alto, Calif.), and pSVβ-gal obtained from Promega Corporation (Madison, Wis.), or synthesized either de novo or by adaptation of a publically or commercially available eukaryotic expression system.

The individual elements within the eukaryotic expression cassette can be derived from multiple sources and may be selected to confer specificity in sites of action or longevity of the cassettes in the recipient cell. Such manipulation of the eukaryotic expression cassette can be done by any standard molecular biology approach.

These cassettes usually are in the form of plasmids, and contain various promoters well-known to be useful for driving expression of genes in animal cells, such as the viral derived SV40, CMV and, RSV promoters or eukaryotic derived β-casein, uteroglobin, β-actin or tyrosinase promoters. The particular promoter is not critical to the present, except in the case where the object is to obtain expression in only selective cell types. In this case, the promoter is selected to be one which is only active in the selected cell type. Examples of tissue specific promoters include, but are not limited to, α S1- and β-casein promoters which are specific for mammary tissue (Platenburg et al, *Trans. Res.*, 3:99–108 (1994) ; and Maga et al, *Trans. Res.*, 3:36–42 (1994)); the phosphoenolpyruvate carboxykinase promoter which is active in liver, kidney, adipose, jejunum and mammary tissue (McGrane et al, *J. Reprod. Fert.*, 41:17–23 (1990)); the tyrosinase promoter which is active in lung and spleen cells, but not testes, brain, heart, liver or kidney (Vile et al, *Canc. Res.*, 54:6228–6234 (1994)); the involucerin promoter which is only active in differentiating keratinocytes of the squamous epithelia (Carroll et al, *J. Cell Sci.*, 103:925–930 (1992)); and the uteroglobin promoter which is active in lung and endometrium (Helftenbein et al, *Annal. N.Y. Acad. Sci.*, 622:69–79 (1991)).

Alternatively, cell specific enhancer sequences can be used to control expression, for example human neurotropic papovirus JCV enhancer regulates viral transcription in glial cells alone (Remenick et al, *J. Virol.*, 65:5641–5646 (1991)). Yet another way to control tissue specific expression is to use a hormone responsive element (HRE) to specify which cell lineages a promoter will be active in, for example, the MMTV promoter requires the binding of a hormone receptor, such as progesterone receptor, to an upstream HRE before it is activated (Beato, *FASEB J.*, 5:2044–2051 (1991); and Truss et al, *J. Steroid Biochem. Mol. Biol.*, 41:241–248 (1992)).

Additional genetic elements may be included on the plasmid in order to modify its behavior inside the recipient animal cell (Hodgson, *Bio/Technology*, 13:222–225 (1995)). Such elements include but are not limited to mammalian artificial chromosome elements or elements from the autonomous replicating circular minichromosomes, such as found in DiFi colorectal cancer cells, to allow stable non-integrated retention of the expression cassette (Huxley et al, *Bio/Technology*, 12:586–590 (1994); and Untawale et al, *Canc. Res.*, 53:1630–1636 (1993)), intergrase to direct integration of the expression cassette into the recipient cells chromosome (Bushman, *Proc. Natl. Acad. Sci., USA*, 91:9233–9237 (1994), the inverted repeats from adeno-associated virus to promote non-homologous integration into the recipient cells chromosome (Goodman et al, *Blood*, 84:1492–1500 (1994), recA or a restriction enzyme to promote homologous recombination (PCT Patent Publication No. WO9322443 (1993); and PCT Patent Publication No. WO9323534-A (1993)) or elements that direct nuclear targeting of the eukaryotic expression cassette (Hodgson, supra; and Lewin, supra). It may be advantageous to encode some of these elements, such as intergrase, recA, and restriction enzymes, in prokaryotic expression cassettes, either on the same genetic element as the eukaryotic expression cassette or alternatively on separate genetic elements. The placing of such toxic or deleterious elements under the control of a prokaryotic promoter ensures that these elements will only be transcribed or translated prior to lysis of the bacterial cell, while the prokaryotic translational and transcriptional machinery is functioning, and thus a finite dose of the element encoded will be delivered to the eukaryotic recipient.

In the present invention, the live invasive bacteria can deliver eukaryotic expression cassettes encoding a gene into an animal cell or animal tissue. The gene may be either a foreign gene or a endogenous gene. As used herein, "foreign gene" means a gene encoding a protein or fragment thereof or anti-sense RNA or catalytic RNA, which is foreign to the recipient animal cell or tissue, such as a vaccine antigen, immunoregulatory agent, or therapeutic agent. An "endogenous gene" means a gene encoding a protein or part thereof or anti-sense RNA or catalytic RNA which is naturally present in the recipient animal cell or tissue.

The vaccine antigen may be a protein or antigenic fragment thereof from viral pathogens, bacterial pathogens, and parasitic pathogens. Alternatively, the vaccine antigen may be a synthetic gene, constructed using recombinant DNA methods, which encode antigens or parts thereof from viral, bacterial, parasitic pathogens. These pathogens can be infectious in humans, domestic animals or wild animal hosts.

The antigen can be any molecule that is expressed by any viral, bacterial, parasitic pathogen prior to or during entry into, colonization of, or replication in their animal host.

Multiple eukaryotic expression cassettes can be delivered that express any combination of viral, bacterial, parasitic antigens, or synthetic genes encoding all or parts or any combination of viral, bacterial, parasitic antigens.

The viral pathogens, from which the viral antigens are derived, include, but are not limited to, Orthomyxoviruses, such as influenza virus; Retroviruses, such as RSV and SIV, Herpesviruses, such as EBV; CMV or herpes simplex virus; Lentiviruses, such as human immunodeficiency virus; Rhabdoviruses, such as rabies; Picornoviruses, such as poliovirus; Poxviruses, such as vaccinia; Rotavirus; and Parvoviruses.

Examples of protective antigens of viral pathogens include the human immunodef iciency virus antigens Nef, p24, gp120, gp41, Tat, Rev, and Pol et al, *Nature*, 313:277–280 (1985)) and T cell and B cell epitopes of gp120 (Palker et al, *J. Immunol.*, 142:3612–3619 (1989)); the hepatitis B surface antigen (Wu et al, *Proc. Natl. Acad. Sci., USA*, 86:4726–4730 (1989)); rotavirus antigens, such as VP4 (Mackow et al, *Proc. Natl. Acad. Sci., USA*, 87:518–522 (1990)) and VP7 (Green et al, *J. Virol.*, 62:1819–1823 (1988)), influenza virus antigens such as hemagglutinin or nucleoprotein (Robinson et al., Supra; Webster et al, Supra) and herpes simplex virus thymidine kinase (Whitley et al, In: *New Generation Vaccines*, pages 825–854).

The bacterial pathogens, from which the bacterial antigens are derived, include but are not limited to, Mycobacterium spp., *Helicobacter pylori*, Salmonella spp., Shigella spp., *E. coli*, Rickettsia spp., Listeria spp., *Legionella pneumoniae*, Pseudomonas spp., Vibrio spp., and *Borellia burgdorferi*.

Examples of protective antigens of bacterial pathogens include the *Shigella sonnei* form 1 antigen (Formal et al, *Infect. Immun.*, 34:746–750 (1981)); the O-antigen of *V. cholerae* Inaba strain 569B (Forrest et al, *J. Infect. Dis.*, 159:145–146 (1989); protective antigens of enterotoxigenic *E. coli*, such as the CFA/I fimbrial antigen (Yamamoto et al, *Infect. Immun.*, 50:925–928 (1985)) and the nontoxic B-subunit of the heat-labile toxin (Clements et al, 46:564–569 (1984)); pertactin of *Bordetella pertussis* (Roberts et al, *Vacc.*, 10:43–48 (1992)), adenylate cyclase-hemolysin of *B. pertussis* (Guiso et al, *Micro. Path.*, 11:423–431 (1991)), and fragment C of tetanus toxin of *Clostridium tetani* (Fairweather et al, *Infect. Immun.*, 58:1323–1326 (1990)).

The parasitic pathogens, from which the parasitic antigens are derived, include but are not limited to, Plasmodium spp., Trypanosome spp., Giardia spp., Boophilus spp., Babesia spp., Entamoeba spp., Eimeria spp., Leishmania spp., Schistosome spp., Brugia spp., Fascida spp., Dirofilaria spp., Wuchereria spp., and Onchocerea spp.

Examples of protective antigens of parasitic pathogens include the circumsporozoite antigens of Plasmodium spp. (Sadoff et al, *Science*, 240:336–337 (1988)), such as the circumsporozoite antigen of *P. bergerii* or the circumsporozoite antigen of *P. falciparum*; the merozoite surface antigen of Plasmodium spp. (Spetzler et al, *Int. J. Pept. Prot. Res.*, 43:351–358 (1994)); the galactose specific lectin of Entamoeba histolytica (Mann et al, *Proc. Natl. Acad. Sci., USA*, 88:3248–3252 (1991)), gp63 of Leishmania spp. (Russell et al, *J. Immunol.*, 140:1274–1278 (1988)), paramyosin of Brugia malayi (Li et al, *Mol. Biochem. Parasitol.*, 49:315–323 (1991)), the triose-phosphate isomerase of *Schistosoma mansoni* (Shoemaker et al, *Proc. Natl. Acad. Sci., USA*, 89:1842–1846 (1992)); the secreted globin-like protein of *Trichostrongylus colubriformis* (Frenkel et al, *Mol. Biochem. Parasitol.*, 50:27–36 (1992)); the glutathione-S-transferase's of *Frasciola hepatica* (Hillyer et al, *Exp. Parasitol.*, 75:176–186 (1992)), *Schistosoma bovis* and *S. japonicum* (Bashir et al, *Trop. Geog. Med.*, 46:255–258 (1994)); and KLH of *Schistosoma bovis* and *S. japonicum* (Bashir et al, supra).

In the present invention, the live invasive bacteria can also deliver eukaryotic expression cassettes encoding a therapeutic agent to animal cells or animal tissue. For example, the eukaryotic expression cassettes can encode tumor-specific, transplant, or autoimmune antigens or parts thereof. Alternatively, the eukaryotic expression cassettes can encode synthetic genes, which encode tumor-specific, transplant, or autoimmune antigens or parts thereof.

Examples of tumor specific antigens include prostate specific antigen (Gattuso et al, *Human Pathol.*, 26:123–126 (1995)), TAG-72 and CEA (Guadagni et al, *Int. J. Biol. Markers*, 9:53–60 (1994)), MAGE-1 and yrosinase (Coulie et al, *J. Immunothera.*, 14:104–109 (1993)). Recently it has been shown in mice that immunization with non-malignant cells expressing a tumor antigen provides a vaccine effect, and also helps the animal mount an immune response to clear malignant tumor cells displaying the same antigen (Koeppen et al, *Anal. N.Y. Acad. Sci.*, 690:244–255 (1993)).

Examples of transplant antigens include the CD3 receptor on T cells (Alegre et al, *Digest. Dis. Sci.*, 40:58–64 (1995)). Treatment with an antibody to CD3 receptor has been shown to rapidly clear circulating T cells and reverse most rejection episodes (Alegre et al, supra).

Examples of autoimmune antigens include IAS β chain (Topham et al, *Proc. Natl. Acad. Sci., USA*, 91:8005–8009 (1994)). Vaccination of mice with an 18 amino acid peptide from IAS β chain has been demonstrated to provide protection and treatment to mice with experimental autoimmune encephalomyelitis (Topham et al, supra).

Alternatively, in the present invention, live invasive bacteria can deliver eukaryotic expression cassettes encoding immunoregulatory molecules. These immunoregulatory molecules include, but are not limited to, growth factors, such as N-CSF, GM-CSF; and cytokines, such as IL-2, IL-4, IL-5, IL-6, IL-10, IL-12 or IFN-γ. Recently, delivery of cytokines expression cassettes to tumor tissue has been shown to stimulate potent systemic immunity and enhanced tumor antigen presentation without producing a systemic cytokine toxicity (Golumbek et al, *Canc. Res.*, 53:5841–5844 (1993); Golumbek et al, *Immun. Res.*, 12:183–192 (1993); Pardoll, *Curr. Opin. Oncol.*, 4:1124–1129 (1992); and Pardoll, *Curr. Opin. Immunol.*, 4:619–623 (1992)).

The antisense RNA and catalytic RNA species delivered to animal cells can be targeted against any molecule present within the recipient cell or likely to be present within the recipient cell. These include but are not limited to RNA species encoding cell regulatory molecules, such as interlukin-6 (Mahieu et al, *Blood*, 84:3758–3765 (1994)), oncogenes such as ras (Kashani-Sabet et al, *Antisen. Res. Devel.*, 2:3–15 (1992)), causitive agents of cancer such as human papillomavirus (Steele et al, *Canc. Res.*, 52:4706–4711 (1992)), enzymes, viral RNA's and pathogen derived RNA's such as HIV-1 (Meyer et al, *Gene*, 129:263–268 (1993); Chatterjee et al, *Sci.*, 258:1485–1488 (1992); and Yamada et al, *Virol.*, 205:121–126 (1994)). The RNAs can also be targeted at non-transcribed DNA sequences, such as promoter or enhancer regions, or to any other molecule present in the recipient cells, such as but not limited to, enzymes involved in DNA synthesis or tRNA molecules (Scanlon et al, *Proc. Natl. Acad. Sci. USA*, 88:10591–10595 (1991); and Baier et al, *Mol. Immunol.*, 31:923–932 (1994)).

In the present invention, live invasive bacteria can also deliver eukaryotic expression cassettes encoding proteins to animal tissue from which they can later be harvested or purified. An example is the delivery of a eukaryotic expression cassette under the control of a mammary specific viral promoter, such as derived from mouse mammary tumor virus (ATCC No. VR731), encoding $\alpha_1$-antitrypsin to mammary tissue of a goat or sheep.

Alternatively an invasive bacteria carrying a eukaryotic expression cassette can be introduced to a tissue site such that it would not spread from such a site. This could be accomplished by any of several methods including delivery of a very limited dose, delivery of a severely attenuated auxotrophic strain, such as an asd mutant (Curtiss et al, supra) that will be rapidly inactivated or die, or delivery of a bacterial strain that contains attenuating lesions, such as a suicide systems (Rennell et al, supra; and Reader et al, supra) under the control of a strong promoter, such as the anerobic nirB promoter (Harborne et al, supra) which will be switched on within the recipient host tissue. Additionally, through use of different species and/or serotypes multiple doses of invasive bacteria, the eukaryotic expression cassette of interest can be given to an animal so as to manipulate expression levels or product type. This approach obviates the need for specially raised transgenic animals containing tissue specific promoters and having tight control of expression, as is currently the case (Janne et al, *Int. J. Biochem.*, 26:859–870 (1994); Mullins et al, *Hyperten.*, 22:630–633 (1993); and Persuy et al, *Eur. J. Bichem.*, 205:887–893 (1992)).

As a further alternative, single or multiple eukaryotic expression cassettes encoding tumor-specific, transplant, and/or autoimmune antigens, can be delivered in any single or multiple combination with eukaryotic expression cassettes encoding immunoregulatory molecules or other proteins.

Yet a further alternative approach is to deliver prokaryotic expression cassettes in combination with eukaryotic expression cassettes.

The invasive bacteria containing the eukaryotic expression cassette can be used to infect animal cells that are cultured in vitro. The animal cells can be further cultured in vitro, and the cells carrying the desired genetic trait can be enriched by selection for or against any selectable marker introduced to the recipient cell at the time of bactofection. Such markers may include antibiotic resistance genes, e.g., hygromycin, or neomycin, selectable cell surface markers, or any other phenotypic or genotypic element introduced or altered by bactofection. These in vitro-infected cells or the in vitro-enriched cells can then be introduced into animals intravenously, intramuscularly, intradermally, or intraperitoneally, or by any inoculation route that allows the cells to enter the host tissue.

Alternatively, the invasive bacteria containing the eukaryotic expression cassettes can be introduced to infect the animal by intravenous, intramuscular, intradermal, intraperitoneally, peroral, intranasal, intraocular, intrarectal, intravaginal, oral, immersion and intraurethral inoculation routes.

The amount of the live invasive bacteria of the present invention to be administered will vary depending on the species of the subject, as well as the disease or condition that is being treated. Generally, the dosage employed will be about $10^3$ to $10^{11}$ viable organisms, preferably about $10^5$ to $10^9$ viable organisms. Alternatively, when bactofecting individual cells, the dosage of viable organisms to administered will be at a multiplicity of infection ranging from about 0.1 to $10^6$, preferably about $10^2$ to $10^4$.

The invasive bacteria of the present invention are generally administered along with a pharmaceutically acceptable carrier or diluent.

The particular pharmaceutically acceptable carrier or diluent employed is not critical to the present invention. Examples of diluents include a phosphate buffered saline, buffer for buffering against gastric acid in the stomach, such as citrate buffer (pH 7.0) containing sucrose, bicarbonate buffer (pH 7.0) alone (Levine et al, *J. Clin. Invest.*, 79:888–902 (1987); and Black et al *J. Infect. Dis.*, 155:1260–1265 (1987)), or bicarbonate buffer (pH 7.0) containing ascorbic acid, lactose, and optionally aspartame (Levine et al, *Lancet*, II:467–470 (1988)). Examples of carriers include proteins, e.g., as found in skim milk, sugars, e.g., sucrose, or polyvinylpyrrolidone. Typically these carriers would be used at a concentration of about 0.1–90% (w/v) but preferably at a range of 1–10% (w/v).

The following examples are provided for illustrative purposes only, and are in no way intended to limit the scope of the present invention.

EXAMPLE 1

Bactofection Requires A Eukaryotic Expression Cassette

The following experiment was carried out to demonstrate that infection with invasive bacteria is able to introduce a foreign gene into animal cells, which is then expressed by the animal cells (hereinafter "bactofection").

A. The Eukarvotic Expression Cassette

An attenuated *Shigella flexneri* strain containing both ΔaroA and ΔvirG attenuating lesions (Noriega et al, supra) was transformed with either pSVβ-gal (Promega Corporation, Madison, Wis.), which contains the reporter gene β-galactosidase (β-gal) (hereinafter "pβ-gal+SV"), or a derivative thereof which lacks the viral derived SV40 eukaryotic promoter region (hereinafter "pβ-gal–SV"), as described by Promega Corp. (TB094, Promega Corp.). Both constructs also contain the prokaryotic *Escherichia coli* gpt promoter which enables expression of β-gal by *S. flexneri*.

pβ-gal–SV was obtained by removing the SV40 promoter from pβ-gal+SV by HindIII and NcoI restriction endonuclease digestion, filling in the DNA overhangs, and then carrying out religation using standard molecular biology techniques (Sambrook et al, supra). The deletion of the SV40 promoter region was confirmed by restriction digest analysis.

Thus, pβ-gal+SV contains a functional eukaryotic expression cassette, whereas pβ-gal–SV only contains a functional prokaryotic promoter.

The resulting transformed bacteria were seeded from 30% (w/v) glycerol stocks, maintained at −70° C., onto solid medium (Tryptic Soy Agar, DIFCO, Madison, Wis.) containing 100 μg/ml of ampicillin, to select for bacteria containing the plasmids, and grown overnight at 37° C.

B. The Eukaryotic Cells

HeLa cells (ATCC No. CCL-2) were grown on plastic tissue culture plates at 37° C. in 5% (v/v) $CO_2$ in RPMI medium supplemented with 10% (v/v) fetal bovine serum, 2.0 mM L-glutamine, 1.0 mM L-pyruvate, 50 U/ml penicillin and 50 μg/ml streptomycin (hereinafter "RPMI/FBS"). 24 to 48 hours prior to bactofection, the HeLa cells were trypsinized with 0.25% (w/v) trypsin containing 1.0 mM EDTA, and split by limiting dilution such that they were 40–60% confluent at the time of the experiment.

Prior to bactofection, the number of HeLa cells present was ascertained by counting in a hemocytometer (Celis, *Cell Biology: A Laboratory Manual*, Ed. Academic Press, San Diego, Calif. (1994)).

C. Bactofection of the Eukaryotic Cells $5 \times 10^4$ HeLa cells were washed once with RPMI media lacking fetal bovine serum and penicillin/streptomycin (hereinafter "SFM"), then overlaid with a bacterial suspension in SFM, and incubated at 37° C. in 5% $CO_2$. The bacterial suspension was either off the overnight agar plates or from a fresh broth culture, and was prepared to give an infection ratio of approximately $10^1$ to $10^3$ viable transformed bacteria to 1 HeLa cell.

After 3 hours, the SFM containing the extra-cellular bacteria was removed, the HeLa cells rinsed once with RPMI/FBS, and then fresh RPMI/FBS containing 100 μg/ml gentamicin was added. Following a further 1 hour incubation at 37° C. in 5% $CO_2$, the gentamicin solution was removed, the HeLa cells rinsed once with RPMI/FBS, fresh RPMI/FBS was added and the cells were returned to 37° C. in 5% $CO_2$.

At 6 hours, 24 hours, 48 hours, 72 hours and 92 hours post-bactofection, the HeLa cells were washed twice with phosphate buffered saline (hereinafter "PBS"), stained for β-gal activity as described by Hawley-Nelson et al, Focus, 15:73–79 (1993), and then photographed. When the incubation time prior to analysis was greater than 48 hours, then the RPMI/FBS was changed at 48 hours.

Cells in which the cytoplasm had stained evenly blue were only observed for HeLa cells bactofected with *S. flexneri* containing pβ-gal+SV, and not for HeLa cells bactofected with *S. flexneri* containing pβ-gal–SV. The average extent of confluent staining was greater the longer the period between bactofection and photography, which indicates that expression was not due solely to β-gal synthesized by the Shigella prior to bactofection, but was a result of newly synthesized β-gal within the HeLa cell. This was confirmed by the pβ-gal–SV bactofected cells in which there was no increase in the extent of staining in relation to time.

The ratio of positive β-gal stained bactofected transformed HeLa cells, defined as those in which greater than 25% of the cytoplasm stained blue (hereafter "transfected"), to non-transformed, but bacterial associated HeLa cells, defined as those with blue stained inter-cytosolic bacteria (a result of *S. flexneri* expression of β-gal off of the *E. coli* gpt promoter) and/or less than or equal to 25% of the cytoplasm stained blue (hereafter "untransfected"), was determined by counting 500 cells in each of 3 wells. In both sets of bactofected cells, a small number ($\leq 5$ per well) of HeLa cells were hyperinfected with *S. flexneri*. These hyperinfected cells were distinguishable by their 'patchy' appearance and non-uniform coloration, due to the individual blue stained bacteria which were visible by microscopy. These hyperinfected cells were not counted as having >25% blue staining. The results are shown in Table 1 below.

TABLE 1

| Time | pβ-gal + SV | | pβ-gal – SV | |
|---|---|---|---|---|
| (h) | untransfected | transfected | untransfected | transfected |
| 6 | 198.33 ± 40.10 | 22.00 ± 2.65 | 161.00 ± 44.64 | 0 |
| 24 | 136.00 ± 17.09 | 69.67 ± 16.62 | 168.33 ± 17.93 | 0 |
| 48 | 121.00 ± 39.59 | 102.00 ± 8.66 | 188.00 ± 12.00 | 0 |
| 72 | 75.67 ± 44.52 | 46.00 ± 22.65 | 96.00 ± 15.10 | 0 |
| 92 | 75.00 ± 19.97 | 39.67 ± 15.96 | 131.33 ± 21.01 | 0 |

As shown in Table 1 above, only HeLa cells bactofected with the eukaryotic SV40 promoter containing β-gal construct (p62 -gal+SV) resulted in a transformed phenotype. This indicates that the blue β-gal phenotype was not due to prokaryotically expressed β-gal, but rather was due to nascent synthesis by the bactofected HeLa cells.

The survival of the attenuated *S. flexneri* inside of the HeLa cells was determined by counting viable bacteria present in each of 3 wells at 6 hours, 24 hours, 48 hours, 72 hours and 92 hours, post-bactofection by standard methods (Celis, *Cell Biology: A Laboratory Manual*, Ed, Academic Press, San Diego Calif. (1994)), i.e., the post-bactofected HeLa cells were lysed with 1.0% (w/v) deoxycholic acid and viable bacteria enumerated on solid media. The results are shown in FIG. 1A for HeLa cells bactofected with *S. flexneri*::pβ-gal+SV, and in FIG. 1B, for HeLa cells bactofected with *S. flexneri*::pβ-gal–SV.

Figure 1A:
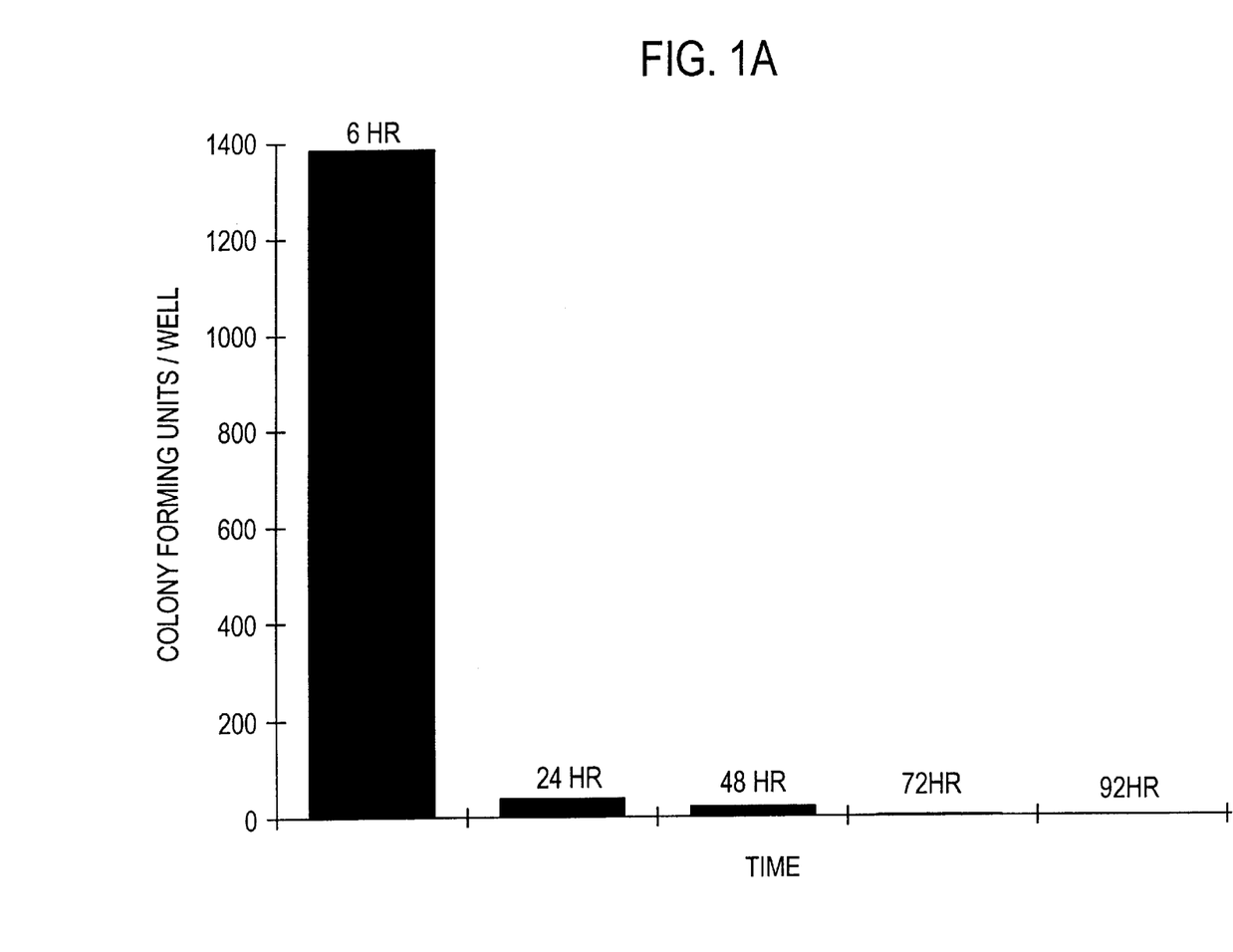
FIGS. 1A and 1B show the colony forming units per well of S. flexneri ΔaroAΔvirG containing the pβ-gal+SV40 expression cassette (FIG. 1A), or containing the pβ-gal-SV40 expression cassette (FIG. 1B), that survive intra-cellularly within HeLa cells 6 hours, 24 hours, 48 hours, 72 hours and 92 hours post-bactofection.
Figure 1B:
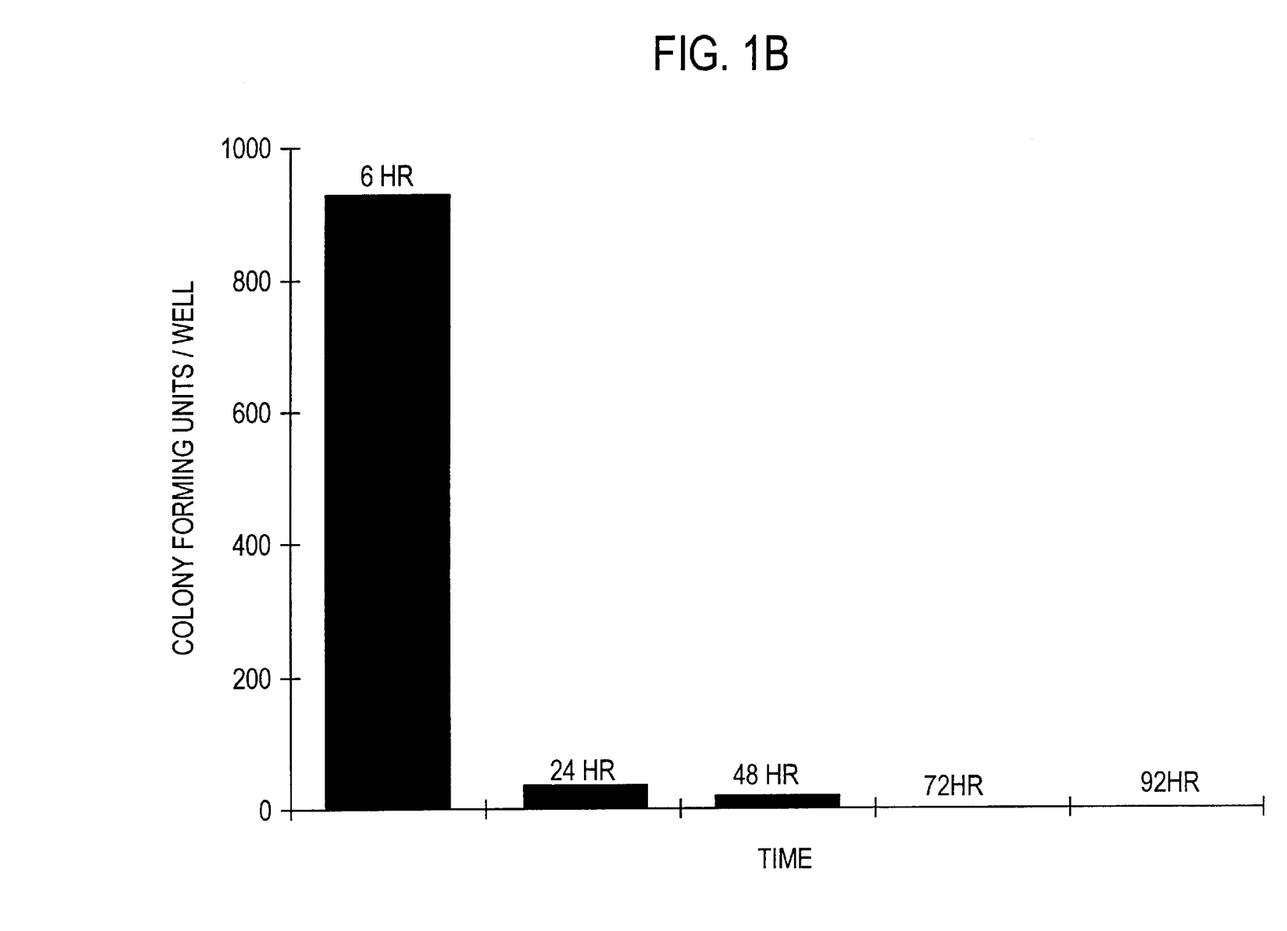

As shown in FIGS. 1A and 1B, the *S. flexneri* were rapidly inactivated inside the HeLa cells. This further demonstrates that the increase in β-gal phenotype is due to new enzyme synthesis. That is, plasmids used in this example are derived from pSVβ-gal and lack a eukaryotic origin of replication. As such they are not replicating inside the recipient HeLa cells. Therefore, the partitioning of the plasmid is not regulated and new daughter cells will not contain sufficient plasmid to develop a permanently transformed phenotype.

To confirm that bactofection was not killing the HeLa cells, control bactofected HeLa cells (using *S. flexneri*::pβ-gal+SV) were counted at regular intervals methods, in a hemocytometer after trypsin treatment as described by Celis, supra. The results, average of 2 wells per time point, are shown in FIG. 2.

Figure 2:
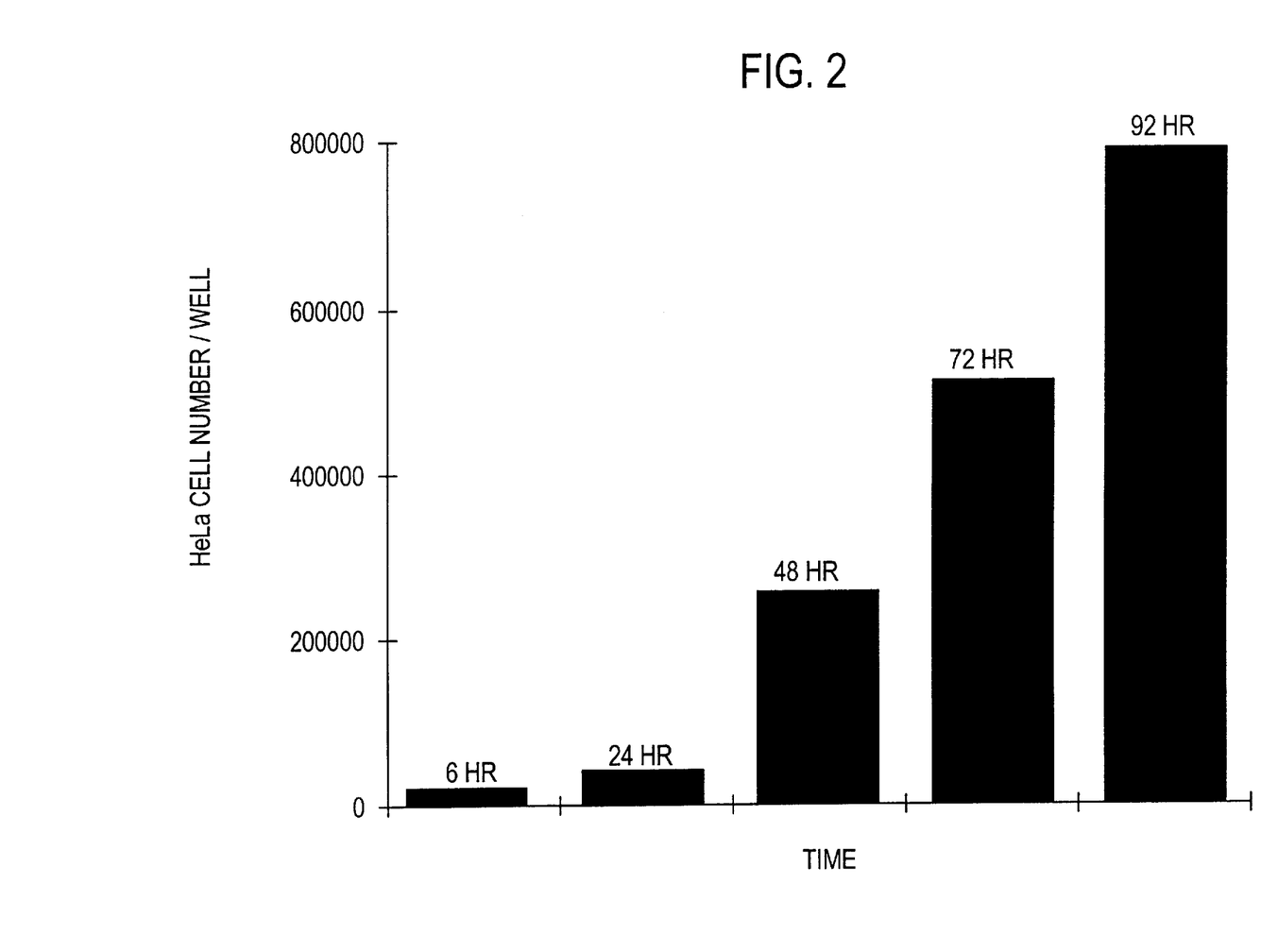
FIG. 2 shows the cell number per well of HeLa cells present 6 hours, 24 hours, 48 hours, 72 hours and 92 hours post-bactofection with S. flexneri ΔaroAΔvirG containing the pβ-gal+SV40 expression cassette.
Figure 3A:
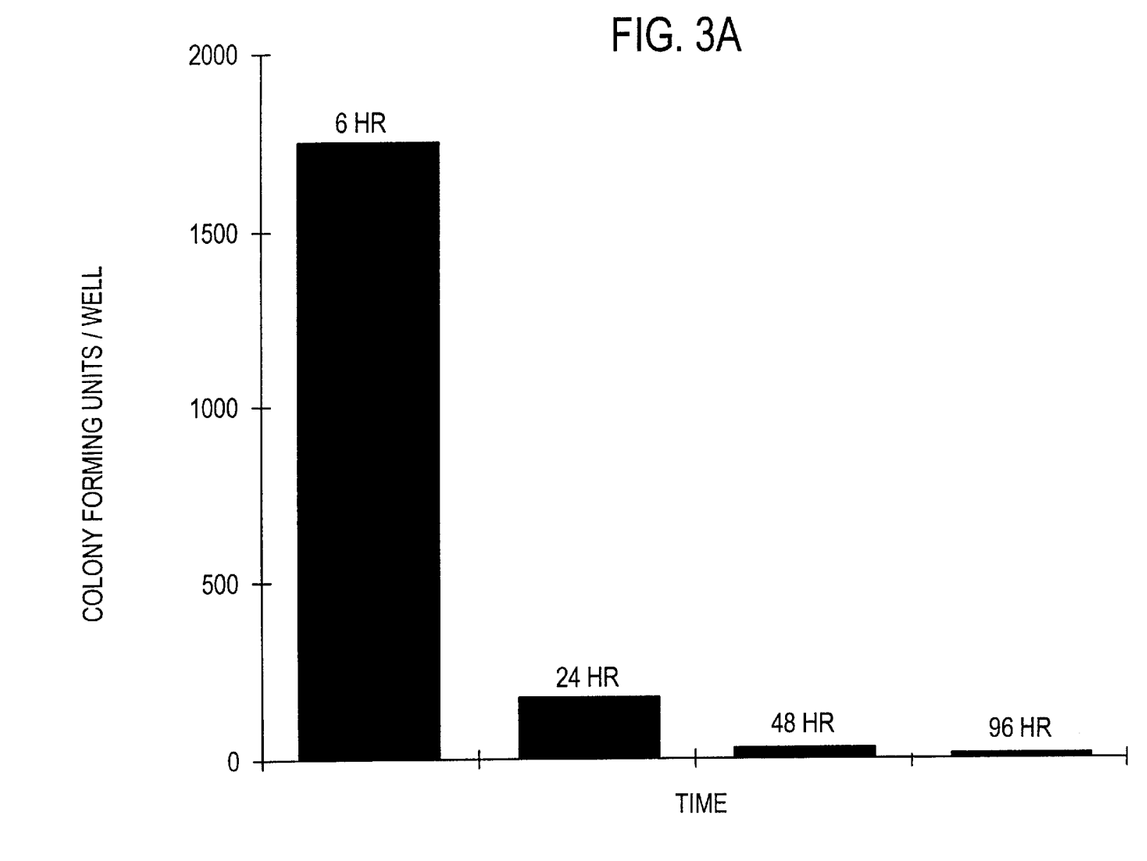
FIGS. 3A and 3B show the colony forming units per well of S. flexneri Δasd containing the pβ-gal+SV40 expression cassette (FIG. 3A), or containing the pβ-gal-SV40 expression cassette (FIG. 3B), that survive intra-cellularly within HeLa cells 6 hours, 24 hours, 48 hours and 96 hours post-bactofection.
Figure 3B:
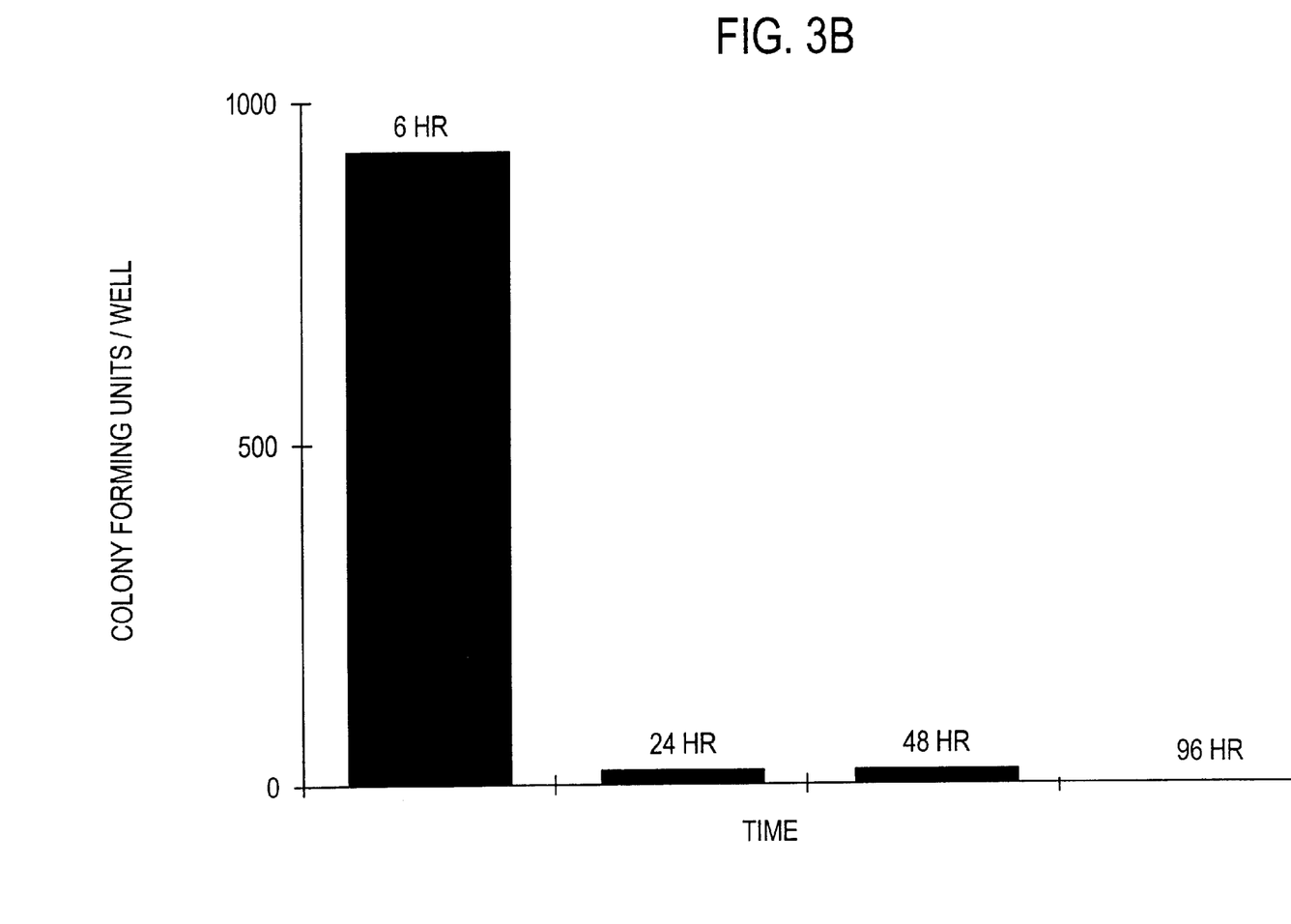
Figure 4:
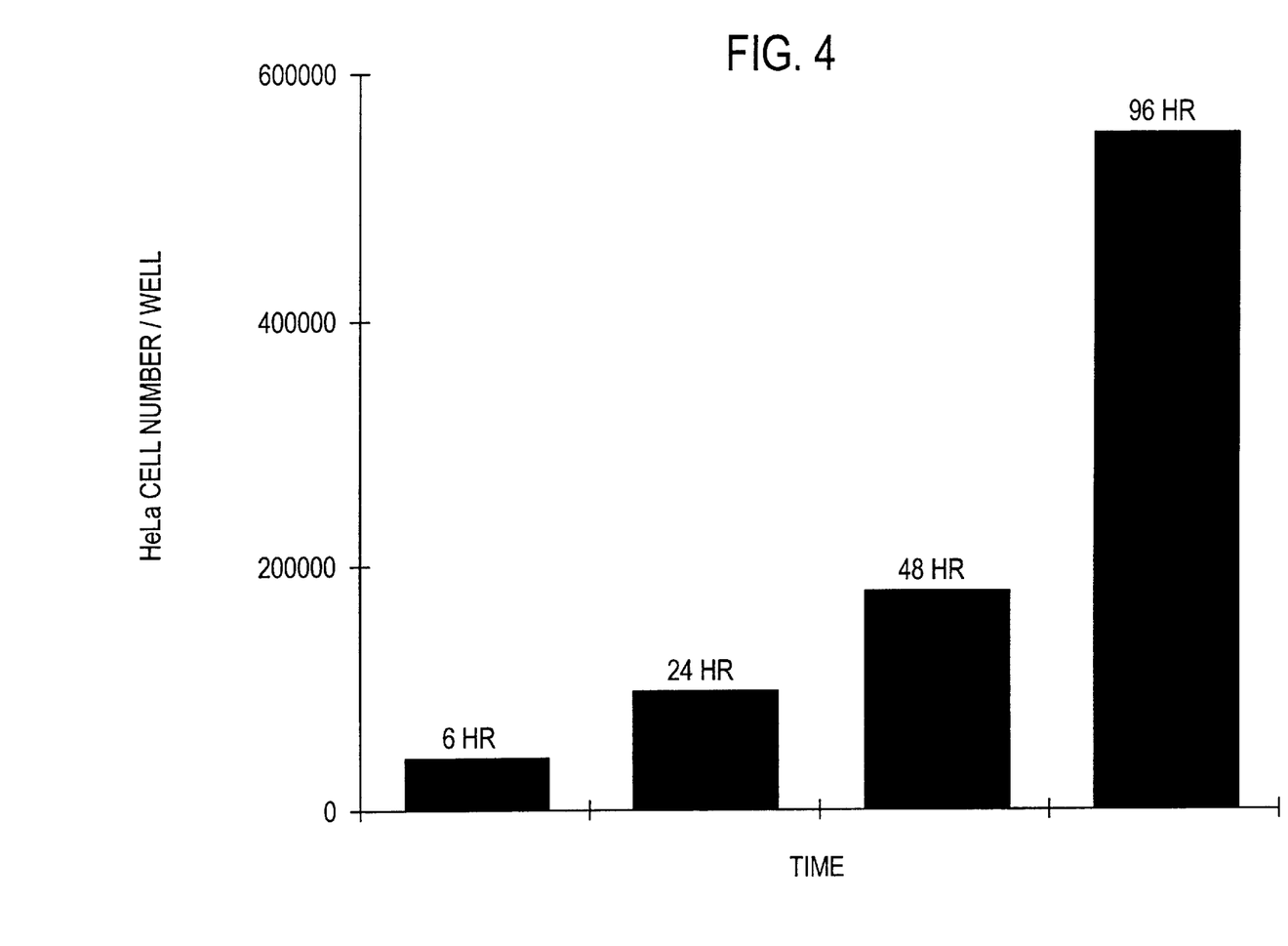
FIG. 4 shows the cell number per well of HeLa cells present 6 hours, 24 hours, 48 hours and 96 hours post-bactofection with S. flexneri Δasd containing the pβ-gal+SV40 expression cassette.

As shown in FIG. 2 the HeLa cell number continued to increase throughout the experiment, indicating that the process of bactofection can be accomplished without significant cellular cytotoxicity against the host cell.

EXAMPLE 2

Bactofection In Various Cell Types

To ascertain the ability of bactofection to transform cell lines other than the epithelial like human cervical HeLa cells, two additional epithelial like cell lines and one kidney cell line were subjected to bactofection.

More specifically, Int 407 (ATCC No. CCL-6), a human fetal ileum/jejunal cell line; CaCo-2 (ATCC No. HTB-37), a human colonic cell line; and MDCK (ATCC No. CCL-34), a canine kidney cell line were cultured and infected with *S. flexneri* containing either pβ-gal+SV or pβ-gal–SV, and evaluated for β-gal activity 24 hours post-bactofection as described in Example 1 above for the HeLa cells.

Using pβ-gal+SV, transformed β-gal positive stained cells were obtained for the Int 407 and CaCo-2 cells, but, as expected, not for the MDCK cells. That is, bactofection appears to mirror the natural invasion characteristics seen by wild-type Shigella sp., as such Shigella very rarely causes infection in dogs, and normally is only found in epithelial cells (Kreig et al, supra).

Thus, it is evident that the method of the present invention is not restricted to one animal cell type, but is applicable to animal cells derived from various tissues.

EXAMPLE 3

Bactofection-Mediated Expression Of Various Foreign Antigens

The following experiment was carried out to demonstrate that bactofection is able to mediate expression of various foreign antigens in HeLa cells, as well as in human peripheral blood derived mononuclear cells.

A. The Eukaryotic Expression Cassette

The *S. flexneri* ΔaroΔvirG strain was transformed with the commercial eukaryotic reporter plasmid pGFP-C1

(Stratagene, La Jolla, Calif.). This plasmid contains a viral derived CMV eukaryotic promoter driving the expression of a gene encoding the Aequorea victoria jellyfish green fluorescent protein (GFP) (Wang et al, Nature, 369:400–403 (1994)). Plasmid pGFP-C1 does not contain a prokaryotic promoter in the correct location to express GFP in the prokaryotic host, i.e., the GFP gene is not located in a functional prokaryotic expression cassette. Only when the plasmid is delivered into eukaryotic cells is GFP produced from its eukaryotic expression cassette.

In addition, a eukaryotic expression cassette was constructed which contains the gp160 region of HIV-1 on the stable episomal eukaryotic plasmid pCEP4 (Invitrogen Corporation, San Diego, Calif.). The plasmid was made by cloning a 3.5 kb PCR amplified XbaI::NotI fragment spanning from exon 1 of tat to the last exon of rev amplified from the HIV-1 molecular clone pBH10 (Ratner et al, supra). This plasmid was designated plasmid pCEP4::gp160. Due to the design of the host plasmid, pCEP4, the cloned gp160 sequence is only expressed inside eukaryotic cells, i.e., it is present in a eukaryotic expression cassette, not a prokaryotic expression cassette.

B. The Eukaryotic Cells

The HeLa cells were obtained and prepared as described in Example 1 above, except that they were grown on glass coverslips for 24 hours prior bactofection.

Mononuclear cells were enriched for macrophages by culturing in RPMI medium supplemented with 10% (v/v) human serum in teflon beakers for 5 days prior to adhering to glass coverslips, for 24 hours, before bactofection.

C. Bactofection of the Eukaryotic Cells

Both the HeLa cells and macrophages were bactofected with the S. flexneri ΔaroΔvirG strain transformed with pGFP-C1, as described in Example 1 above. 48 hours post-bactofection, the presence of GFP synthesized by the bactofected transformed animal cells was visualized for green fluorescence by fluorescent microscopy. Both HeLa cells and macrophages resulted in two populations, those cells that were bactofected, and therefore fluorescent due to expressed GFP, and those cells that had not been bactofected, and were thereby non-fluorescent. The ratio of bactofected HeLa cells to non-bactofected HeLa cells was visibly similar to that seen with pβ-gal+SV, while it appeared that less macrophages had been bactofected.

In addition, HeLa cells grown on glass coverslips were bactofected, as described in Example 1 above, using Shigella ΔaroΔvirG transformed with either the pCEP4::gp160 or pCEP4. 48 and 72 hours post-bactofection, the coverslips were removed from the RPMI/FBS, rinsed twice with PBS, and then fixed for more than 2 hours in methanol at −20° C. Following fixing, gp160 protein was detected by immunofluorescence using an anti-gp160 monoclonal antibody cocktail (Abacioglu et al, AIDS Res. and Human Retroviruses, 10(4):371–381 (1994)), and a FITC-labeled detector antibody as described by Harlow et al, Antibodies, Cold Spring Harbor Laboratory Press, Cold Spring Harbor, N.Y. (1988). When visualized by fluorescent microscopy, two cell populations were visible, i.e., both positive staining bactofected transformed gp160 expressing cells and non-transformed cells. The ratio of bactofected HeLa cells to non-bactofected HeLa cells was visibly similar to that seen with pβ-gal+SV. However, due to the overexpression of gp160, transformed cells appeared deformed and were essentially unstable for long periods of time.

EXAMPLE 4

Bactofection With Other Attenuating Lesions

In order to demonstrate that the ΔaroΔvirG attenuation in the S. flexneri strain employed in Example 1 is not essential for bactofection, a second S. flexneri strain carrying a Δasd attenuation was transformed with the pβ-gal+SV and pβ-gal−SV plasmids, and used in bactofection experiments of various cell types as described in Example 1.

The Δasd attenuation (EC 1.2.1.11) stops production of peptidoglycans necessary for cell wall synthesis in prokaryotes (Cohen et al, In: Escherichia coli and Salmonella typhimurium: Cellular and Molecular Biology, Vol. 1, pages 429–444, Ingraham et al, Eds., *American Society of Microbiology*, Washington, D.C. (1987)). In the absence of externally added DL-α,∈-diaminopimelic acid (hereinafter "DAP") to the growth media, the Δasd attenuated prokaryotic cells lyse. This compound is not present inside eukaryotic cells.

The presence of the Δasd attenuation resulted in a slightly decreased ability to invade HeLa, Int-407 and CaCo-2 cells compared with the ΔaroΔvirG strain. This attenuated strain was also found to be unable to invade MDCK cells. Addition of DAP (50 μg/ml) to the bacterial cell suspension during the 3 hour invasion incubation restored invasion levels to that seen with the ΔaroΔvirG attenuated strain (see Table 2 below).

TABLE 2

| +/− | pβ-gal + SV | | pβ-gal − SV | |
|---|---|---|---|---|
| DAP | untransfected | transfected | untransfected | transfected |
| +DAP | 135.67 ± 43.32 | 87.66 ± 11.06 | 71.67 ± 16.92 | 0 |
| −DAP | 45.33 ± 14.01 | 43.33 ± 13.20 | 9.00 ± 2.65 | 0 |

Table 2 above shows the number of HeLa cells displaying a transformed phenotype 48 hours after bactofection by *S. flexneri* Δasd transformants with or without added DAP. The cells were stained overnight for β-gal activity, and then 500 cells in each of 3 wells were counted. Averages±std. error are given. Only HeLa cells bactofected with *S. flexneri* Δasd containing pβ-gal+SV resulted in a blue β-gal positive phenotype.

Thus, the nature of the attenuation is not crucial for bactofection to occur, but may influence the level of transformation.

The survival of the attenuated *S. flexneri* Δasd (+DAP) inside of the HeLa cells was determined by counting viable bacteria present in each of 3 wells at 6 hours, 24 hours, 48 hours and 96 hours, post-bactofection as described in Example 1. The results are shown in FIG. 3A for HeLa cells bactofected with *S. flexneri*::pβ-gal+SV, and in FIG. 3B, for HeLa cells bactofected with *S. flexneri*::pβ-gal−SV. As shown in FIGS. 3A and 3B, the *S. flexneri* were not replicating inside the HeLa cells, and therefore the increase in β-gal phenotype must be due to new enzyme synthesis.

To confirm that bactofection was not killing the HeLa cells, control bactofected HeLa cells (using *S. flexneri*::pβ-gal+SV) were counted as described in Example 1. The results, i.e., average of 2 wells per time point, are shown in FIG. 4.

As shown in FIG. 4 the HeLa cell number continued to increase throughout the experiment, indicating that the process of bactofection was not cell cytotoxic.

EXAMPLE 5

Delivery of a Reporter Gene In Vivo to Animal Tissue

In order to demonstrate that bactofection can occur in vivo, restrained mice (Balb/c) were intranasally inoculated with 5×10⁶ viable *S. flexneri* ΔaroΔvirG containing either pβ-gal+SV or pβ-gal−SV in a volume of 10 μl of PBS. 48 hours after inoculation, the mice were sacrificed, lung tissue collected and frozen to −70° C. Cryosections (5.0 μM) were prepared, fixed, and then stained overnight for β-gal activity as described above (Hawley-Nelson et al, supra). Following staining, the sections were rinsed twice with PBS, then sealed under coverslips.

Blue-staining β-gal-positive cells were visible per lung section infected with pβ-gal+SV, but not those infected with pβ-gal−SV.

Thus, bactofection is not a phenomena limited to in vitro applications, but is also suitable for in vivo use.

EXAMPLE 6

Bactofection Requires Both Viability and an Invasion Phenotype

To determine if either viability or an active invasion phenotype are required for bactofection to occur, HeLa cells were bactofected using non-invasive (congo red negative) *S. flexneri* ΔaroΔvirG::pβ-gal+SV and UV-killed invasive (congo red positive) *S. flexneri* ΔaroΔvirG::pβ-gal+SV, as described in Example 1. A duplicate culture, not UV-killed, of the invasive (congo red positive) *S. flexneri* ΔaroΔvirG::pβ-gal+SV was used as a control.

Neither the congo red negative nor the UV-killed bacteria were able to attach to HeLa cells nor invade. In both cases, no positive β-gal stained transformed HeLa cells were detected (see Table 3 below). Additional experiments using either viable congo red positive *S. flexneri* Δasd::pβ-gal+SV (+DAP) or UV-killed (+DAP) cells showed the same result (see Table 3 below).

TABLE 3

| strains containing pβ-gal + SV | untransfected | transfected |
|---|---|---|
| *S. flexneri* ΔaroΔvirG; CR⁺ | 35.00 ± 6.56 | 66.67 ± 1.15 |
| *S. flexneri* ΔaroΔvirG; CR⁺, UV-killed | 1.67 ± 2.08 | 0 |
| *S. flexneri* ΔaroΔvirG; CR⁻ | 6.00 ± 2.00 | 0 |
| *S. flexneri* Δasd; CR⁺ | 135.67 ± 43.32 | 87.66 ± 11.06 |
| *S. flexneri* Δasd; CR⁺, UV-killed | 2.33 ± 4.04 | 0 |

Table 3 above shows the number of HeLa cells displaying a transformed phenotype 48 hours after bactofection by *S. flexneri* strains containing the reporter plasmid pβ-gal+SV. The cells were stained overnight for β-gal activity, and then 500 cells in each of three wells counted. Averages ±std. error are given. Only HeLa cells bactofected with invasive, viable *S. flexneri* resulted in a blue β-gal positive phenotype.

Therefore, the viability and the ability of the prokaryotic cells used in bactofection to invade the eukaryotic target cell appear to be essential for transformation of an animal cell by bactofection.

EXAMPLE 7

Development of an Immune Response to an In Vivo Delivered Gene

In order to show another example of in vivo use of bactofection, 5×10⁷ *S. flexneri* Δaro ΔvirG containing the pCEP4::gp160 plasmid construct were administered intranasally to restrained Balb/c mice. 14 days following bactofection, the mice were sacrificed and spleens collected. Proliferation assays on the spleenocytes were performed by standard methods (Kruisbeck et al, In: *Current Protocols in Immunology*, pages 3.12.1–3.12.4, Current Protocols, New York, N.Y. (1991)) using gp120 (Intracel, Cambridge, Mass.) as a matched antigen and ovalbumin (Sigma Chemical Co., St Louis, Mo.) as control antigen.

Splenocytes isolated from mice bactofected with plasmid pCEP4::gp160, containing the gene for HIV-1 gp160, showed a seven-fold stimulation, while splenocytes from control (pCEP4) bactofected mice showed no response.

Thus bactofection is a suitable system for delivery of genes encoding antigens to which an immune response is mounted.

While the invention has been described in detail, and with reference to specific embodiments thereof, it will be apparent to one of ordinary skill in the art that various changes and modifications can be made therein without departing from the spirit and scope thereof.

What is claimed:

1. A method for introducing and expressing a gene in animal cells comprising infecting said animal cells with live invasive bacteria, wherein said bacteria contain a eukaryotic expression cassette encoding said gene, wherein said gene is expressed at detectable levels, and wherein said animals cells are cultured in vitro.

2. The method of claim 1, wherein said animal cells are mammalian cells.

3. The method of claim 2, wherein said mammalian cells are selected from the group consisting of human, bovine, ovine, porcine, feline, buffalo, canine, goat, equine, donkey, deer, and primate cells.

4. The method of claim 3, wherein said mammalian cells are human cells.

5. The method of claim 1, wherein said invasive bacteria are selected from the group consisting of Shigella spp, Listeria spp., Rickettsia spp and enteroinvasive *Escherichia coli*.

6. The method of claim 5, wherein said invasive bacteria are Shigella spp.

7. The method of claim 6, wherein said Shigella spp. are *Shigella flexneri*.

8. The method of claim 5, wherein said invasive bacteria are attenuated.

9. The method of claim 1, wherein said invasive bacteria are selected from the group consisting of Yersinia spp., Escherichia spp., Klebsiella spp., Bordetella spp., Neisseria spp., Aeromonas spp., Franciesella spp., Corynebacterium spp., Citrobacter spp., Chlamydia spp., Hemophilus spp., Brucella spp., Mycobacterium spp., Legionella spp., Rhodococcus spp., Pseudomonas Spp., Helicobacter spp., Salmonella spp., Vibrio spp., Bacillus spp., Leishmania spp. and Erysipelothrix spp. which have been genetically engineered to mimic the invasion properties of Shigella spp., Listeria spp., Rickettsia spp., or enteroinvasive *E. coli* spp.

10. The method of claim 9, wherein said invasive bacteria are attenuated.

11. The method of claim 1, wherein said animal cells are infected with about $10^3$ to $10^{11}$ viable invasive bacteria.

12. The method of claim 11, wherein said animal cells are infected with about $10^5$ to $10^9$ viable invasive bacteria.

13. The method of claim 1, wherein said animal cells are infected at a multiplicity of infection ranging from about 0.1 to $10^6$.

14. The method of claim 13, wherein said animal cells are infected at a multiplicity of infection ranging from about $10^2$ to $10^4$.

15. The method of claim 1, wherein said gene encodes a member selected from the group consisting of a therapeutic protein, immunoregulatory molecule, antisense RNA, and catalytic RNA.

* * * * *